(12) United States Patent
Sanghvi et al.

(10) Patent No.: US 9,669,096 B2
(45) Date of Patent: *Jun. 6, 2017

(54) STABLE PHARMACEUTICAL FORMULATIONS OF METHYLNALTREXONE

(71) Applicant: Progenics Pharmaceuticals, Inc., Tarrytown, NY (US)

(72) Inventors: Suketu P. Sanghvi, Kendall Park, NJ (US); Thomas A. Boyd, Grandview, NY (US)

(73) Assignee: Progenics Pharmaceuticals, Inc., Tarrytown, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/039,866

(22) Filed: Sep. 27, 2013

(65) Prior Publication Data

US 2014/0235664 A1 Aug. 21, 2014

Related U.S. Application Data

(63) Continuation of application No. 12/639,892, filed on Dec. 16, 2009, now abandoned, which is a continuation of application No. 10/821,811, filed on Apr. 8, 2004, now abandoned.

(60) Provisional application No. 60/461,611, filed on Apr. 8, 2003.

(51) Int. Cl.
| | | |
|---|---|---|
| *A61K 31/485* | (2006.01) | |
| *A61K 47/02* | (2006.01) | |
| *A61K 9/00* | (2006.01) | |
| *A61K 9/19* | (2006.01) | |
| *A61K 31/047* | (2006.01) | |
| *A61K 31/195* | (2006.01) | |
| *A61K 45/06* | (2006.01) | |
| *A61K 47/12* | (2006.01) | |
| *A61K 47/18* | (2017.01) | |

(52) U.S. Cl.
CPC ............ *A61K 47/02* (2013.01); *A61K 9/0019* (2013.01); *A61K 9/19* (2013.01); *A61K 31/047* (2013.01); *A61K 31/195* (2013.01); *A61K 31/485* (2013.01); *A61K 45/06* (2013.01); *A61K 47/12* (2013.01); *A61K 47/18* (2013.01); *A61K 47/183* (2013.01)

(58) Field of Classification Search
None
See application file for complete search history.

(56) References Cited

U.S. PATENT DOCUMENTS

| | | |
|---|---|---|
| 3,714,159 A | 1/1973 | Janssen et al. |
| 3,723,440 A | 3/1973 | Freter et al. |
| 3,854,480 A | 12/1974 | Zaffaroni |
| 3,884,916 A | 5/1975 | Janssen et al. |
| 3,937,801 A | 2/1976 | Lippmann |
| 3,996,214 A | 12/1976 | Dajani et al. |
| 4,012,393 A | 3/1977 | Markos et al. |
| 4,013,668 A | 3/1977 | Adelstein et al. |
| 4,025,652 A | 5/1977 | Diamond et al. |
| 4,060,635 A | 11/1977 | Diamond et al. |
| 4,066,654 A | 1/1978 | Adelstein et al. |
| 4,069,223 A | 1/1978 | Adelstein |
| 4,072,686 A | 2/1978 | Adelstein et al. |
| 4,115,400 A | 9/1978 | Zimmerman |
| 4,115,564 A | 9/1978 | Diamond et al. |
| 4,116,963 A | 9/1978 | Adelstein |
| 4,125,531 A | 11/1978 | Yen |
| 4,176,186 A | 11/1979 | Goldberg et al. |
| 4,194,045 A | 3/1980 | Adelstein |
| 4,203,920 A | 5/1980 | Diamond et al. |
| 4,241,066 A | 12/1980 | Kobylecki et al. |
| 4,277,605 A | 7/1981 | Buyniski et al. |
| 4,311,833 A | 1/1982 | Namikoshi et al. |
| 4,322,426 A * | 3/1982 | Hermann et al. ............. 514/282 |
| 4,326,074 A | 4/1982 | Diamond et al. |
| 4,326,075 A | 4/1982 | Diamond et al. |
| 4,377,568 A | 3/1983 | Chopra |
| 4,385,078 A | 5/1983 | Onda et al. |
| 4,427,676 A | 1/1984 | White et al. |
| 4,430,327 A | 2/1984 | Frederickson |
| 4,452,775 A | 6/1984 | Kent |
| 4,457,907 A | 7/1984 | Porter |
| 4,462,839 A | 7/1984 | McGinley et al. |
| 4,466,968 A | 8/1984 | Bernstein |
| 4,518,433 A | 5/1985 | McGinley et al. |
| 4,533,739 A | 8/1985 | Pitzele et al. |
| 4,556,552 A | 12/1985 | Porter et al. |
| 4,606,909 A | 8/1986 | Bechgaard et al. |
| 4,615,885 A | 10/1986 | Nakagame et al. |
| 4,670,287 A | 6/1987 | Tsuji |
| 4,675,189 A | 6/1987 | Kent et al. |
| 4,689,332 A | 8/1987 | McLaughlin et al. |
| 4,719,215 A | 1/1988 | Goldberg |
| 4,730,048 A | 3/1988 | Portoghese |
| 4,765,978 A | 8/1988 | Abidi et al. |
| 4,806,556 A | 2/1989 | Portoghese |
| 4,824,853 A | 4/1989 | Wals et al. |
| 4,836,212 A | 6/1989 | Schmitt et al. |

(Continued)

FOREIGN PATENT DOCUMENTS

| | | |
|---|---|---|
| AU | 610 561 B2 | 8/1988 |
| AU | 99/13802 | 3/2003 |

(Continued)

OTHER PUBLICATIONS

Remington's Pharmaceutical Sciences pp. 187-189, 257, 1102, 1106, 1107, 1493 and 1523 (1985).*

(Continued)

*Primary Examiner* — Kortney L Klinkel
*Assistant Examiner* — William Lee
(74) *Attorney, Agent, or Firm* — McCarter & English, LLP; Jonathan M. Sparks; Maneesh Gulati

(57) ABSTRACT

Stable pharmaceutical compositions useful for administering methylnaltrexone are described, as are methods for making the same. Kits, including these pharmaceutical compositions, also are provided.

39 Claims, 3 Drawing Sheets

(56) References Cited

U.S. PATENT DOCUMENTS

| | | |
|---|---|---|
| 4,837,214 A | 6/1989 | Tanaka et al. |
| 4,857,833 A | 8/1989 | Gonzalez et al. |
| 4,861,781 A | 8/1989 | Goldberg |
| 4,863,928 A | 9/1989 | Atkinson et al. |
| 4,867,979 A | 9/1989 | Sheth et al. |
| 4,870,084 A | 9/1989 | Eggler et al. |
| 4,883,805 A | 11/1989 | Kasan et al. |
| 4,888,346 A | 12/1989 | Bihari et al. |
| 4,891,379 A | 1/1990 | Zimmerman et al. |
| 4,912,114 A | 3/1990 | Revesz |
| 4,965,269 A | 10/1990 | Brandstrom et al. |
| 4,987,136 A | 1/1991 | Kreek et al. |
| 4,990,521 A | 2/1991 | Van Daele et al. |
| 4,999,342 A | 3/1991 | Ahmad et al. |
| 5,102,887 A | 4/1992 | Goldberg |
| 5,116,868 A | 5/1992 | Chen et al. |
| 5,133,974 A | 7/1992 | Paradissis et al. |
| 5,159,081 A | 10/1992 | Cantrell et al. |
| 5,202,159 A | 4/1993 | Chen et al. |
| 5,220,017 A | 6/1993 | Bock et al. |
| 5,236,947 A | 8/1993 | Calvet et al. |
| 5,250,542 A | 10/1993 | Cantrell et al. |
| 5,256,154 A | 10/1993 | Liebert et al. |
| 5,270,328 A | 12/1993 | Cantrell et al. |
| 5,312,899 A | 5/1994 | Schiller |
| 5,358,970 A | 10/1994 | Ruff et al. |
| 5,391,372 A | 2/1995 | Campbell |
| 5,407,686 A | 4/1995 | Patel et al. |
| 5,426,112 A | 6/1995 | Zagon et al. |
| 5,434,171 A | 7/1995 | Frank et al. |
| 5,472,943 A | 12/1995 | Crain et al. |
| 5,512,578 A | 4/1996 | Crain et al. |
| 5,536,507 A | 7/1996 | Abramowitz et al. |
| 5,567,423 A | 10/1996 | Ying |
| 5,585,348 A | 12/1996 | Crain et al. |
| 5,591,433 A | 1/1997 | Michael et al. |
| 5,597,564 A | 1/1997 | Ying |
| 5,609,871 A | 3/1997 | Michael et al. |
| 5,614,219 A | 3/1997 | Wunderlich et al. |
| 5,614,222 A | 3/1997 | Kaplan |
| 5,626,875 A | 5/1997 | Ballester Rodes et al. |
| 5,629,001 A | 5/1997 | Michael et al. |
| 5,656,290 A | 8/1997 | Kelm et al. |
| 5,686,072 A | 11/1997 | Uhr et al. |
| 5,714,586 A | 2/1998 | Kunstmann et al. |
| 5,739,152 A | 4/1998 | Andersson et al. |
| 5,767,125 A | 6/1998 | Crain et al. |
| 5,804,595 A | 9/1998 | Portoghese et al. |
| 5,811,451 A | 9/1998 | Minoia et al. |
| 5,821,219 A | 10/1998 | Grandy et al. |
| 5,866,154 A * | 2/1999 | Bahal et al. ............... 424/423 |
| 5,866,164 A | 2/1999 | Kuczynski et al. |
| 5,958,452 A | 9/1999 | Oshlack et al. |
| 5,972,954 A | 10/1999 | Foss et al. |
| 5,981,185 A | 11/1999 | Matson et al. |
| RE36,547 E | 2/2000 | Crain et al. |
| 6,025,154 A | 2/2000 | Li et al. |
| 6,096,756 A | 8/2000 | Crain et al. |
| 6,096,763 A | 8/2000 | Hoffman et al. |
| 6,096,764 A | 8/2000 | Bryant et al. |
| 6,099,853 A | 8/2000 | Hertelendy et al. |
| 6,136,780 A | 10/2000 | Zagon et al. |
| 6,143,795 A | 11/2000 | Moschner et al. |
| 6,153,620 A | 11/2000 | Kornetsky |
| 6,190,691 B1 | 2/2001 | Mak |
| 6,194,382 B1 | 2/2001 | Crain et al. |
| 6,261,599 B1 | 7/2001 | Oshlack et al. |
| 6,274,591 B1 | 8/2001 | Foss et al. |
| 6,277,384 B1 | 8/2001 | Kaiko et al. |
| 6,353,004 B1 | 3/2002 | Farrar et al. |
| 6,359,111 B1 | 3/2002 | Meyer et al. |
| 6,362,194 B1 | 3/2002 | Crain et al. |
| 6,384,044 B1 | 5/2002 | Bihari |
| 6,395,705 B2 | 5/2002 | Crain et al. |
| 6,419,959 B1 | 7/2002 | Walter et al. |
| 6,426,094 B2 | 7/2002 | Piver et al. |
| 6,451,806 B2 | 9/2002 | Farrar |
| 6,455,537 B1 | 9/2002 | Cooper |
| 6,469,030 B2 | 10/2002 | Farrar et al. |
| 6,479,500 B1 | 11/2002 | Fukushima et al. |
| 6,559,158 B1 * | 5/2003 | Foss et al. ............... 514/282 |
| 6,608,075 B2 | 8/2003 | Foss et al. |
| 6,693,125 B2 | 2/2004 | Borisy et al. |
| 6,696,066 B2 | 2/2004 | Kaiko et al. |
| 6,720,336 B2 | 4/2004 | Liras |
| 6,723,712 B2 | 4/2004 | Bourhis et al. |
| 6,734,188 B1 | 5/2004 | Rhodes et al. |
| 6,756,364 B2 | 6/2004 | Barbier et al. |
| 6,777,534 B1 | 8/2004 | Klagsbrun et al. |
| 6,794,370 B2 | 9/2004 | Achterrath |
| 6,800,639 B2 | 10/2004 | Giles et al. |
| 6,833,349 B2 | 12/2004 | Xia et al. |
| 6,838,469 B2 | 1/2005 | Sumegi |
| 6,884,879 B1 | 4/2005 | Baca et al. |
| 6,900,234 B1 | 5/2005 | Fossa |
| 6,946,556 B1 | 9/2005 | Likhotvorik et al. |
| 6,960,596 B2 | 11/2005 | Bissery |
| 6,967,016 B2 | 11/2005 | van Gemen et al. |
| 6,984,403 B2 | 1/2006 | Hagen et al. |
| 6,986,901 B2 | 1/2006 | Meisel et al. |
| 6,989,383 B1 | 1/2006 | Rosen et al. |
| 6,992,106 B2 | 1/2006 | Morinaga et al. |
| 7,012,100 B1 | 3/2006 | Edwards et al. |
| 7,074,825 B2 | 7/2006 | Mo et al. |
| 7,094,775 B2 | 8/2006 | Strugnell et al. |
| 7,129,265 B2 | 10/2006 | Mason |
| 7,132,554 B2 | 11/2006 | Rose |
| 7,141,554 B2 | 11/2006 | Rochat et al. |
| 7,160,913 B2 | 1/2007 | Schneider |
| 7,183,269 B2 | 2/2007 | Kreutz |
| 7,196,115 B2 | 3/2007 | Khanuja et al. |
| 7,259,233 B2 | 8/2007 | Dodd et al. |
| 7,501,434 B2 | 3/2009 | Shah et al. |
| 7,563,899 B2 | 7/2009 | Boyd et al. |
| 7,674,904 B2 * | 3/2010 | Doshan ............... C07D 489/08 546/44 |
| 8,343,992 B2 | 1/2013 | Doshan et al. |
| 8,552,025 B2 * | 10/2013 | Sanghvi et al. ............... 514/282 |
| 2001/0010919 A1 | 8/2001 | Grandy et al. |
| 2001/0018413 A1 | 8/2001 | Crain et al. |
| 2001/0033865 A1 | 10/2001 | Oshlack et al. |
| 2001/0036469 A1 | 11/2001 | Gooberman |
| 2001/0036476 A1 | 11/2001 | Oshlack et al. |
| 2001/0036951 A1 | 11/2001 | Farrar et al. |
| 2001/0046968 A1 | 11/2001 | Zagon et al. |
| 2001/0047005 A1 | 11/2001 | Farrar |
| 2002/0028825 A1 | 3/2002 | Foss et al. |
| 2002/0064771 A1 | 5/2002 | Zhong et al. |
| 2002/0068712 A1 | 6/2002 | Stevens |
| 2002/0173466 A1 | 11/2002 | Crain et al. |
| 2002/0176888 A1 | 11/2002 | Bartholomaeus et al. |
| 2002/0188005 A1 | 12/2002 | Farrar et al. |
| 2003/0018043 A1 | 1/2003 | Cooper |
| 2003/0022909 A1 * | 1/2003 | Moss et al. ............... 514/282 |
| 2003/0026801 A1 | 2/2003 | Weiner et al. |
| 2003/0039689 A1 | 2/2003 | Chen et al. |
| 2003/0065003 A1 | 4/2003 | Foss et al. |
| 2003/0096839 A1 * | 5/2003 | Floyd et al. ............... 514/307 |
| 2003/0105121 A1 | 6/2003 | Bihari |
| 2003/0124086 A1 | 7/2003 | Bentley et al. |
| 2003/0144312 A1 | 7/2003 | Schoenhard |
| 2003/0158220 A1 | 8/2003 | Foss et al. |
| 2003/0187010 A1 | 10/2003 | Foss et al. |
| 2003/0191147 A1 | 10/2003 | Sherman et al. |
| 2003/0219406 A1 | 11/2003 | Schroit et al. |
| 2003/0229111 A1 | 12/2003 | Oshlack et al. |
| 2004/0010996 A1 | 1/2004 | Karlstrom et al. |
| 2004/0010997 A1 | 1/2004 | Close |
| 2004/0010998 A1 | 1/2004 | Turco |
| 2004/0024006 A1 | 2/2004 | Simon |
| 2004/0136908 A1 | 7/2004 | Olson et al. |
| 2004/0162306 A1 | 8/2004 | Foss et al. |
| 2004/0162307 A1 | 8/2004 | Foss et al. |
| 2004/0162308 A1 | 8/2004 | Foss et al. |

(56) References Cited

U.S. PATENT DOCUMENTS

| | | |
|---|---|---|
| 2004/0167147 A1 | 8/2004 | Foss et al. |
| 2004/0167148 A1 | 8/2004 | Foss et al. |
| 2004/0180916 A1 | 9/2004 | Levine |
| 2004/0242523 A1 | 12/2004 | Weichselbaum et al. |
| 2004/0254156 A1 | 12/2004 | Le Bourdonnec et al. |
| 2004/0254208 A1 | 12/2004 | Weber et al. |
| 2004/0259898 A1 | 12/2004 | Moss |
| 2004/0259899 A1 | 12/2004 | Sanghvi et al. |
| 2004/0266806 A1 | 12/2004 | Sanghvi et al. |
| 2005/0004029 A1 | 1/2005 | Garcia |
| 2005/0004155 A1 | 1/2005 | Boyd et al. |
| 2005/0011468 A1 | 1/2005 | Moss |
| 2005/0048117 A1 | 3/2005 | Foss et al. |
| 2005/0085514 A1 | 4/2005 | Cosford et al. |
| 2005/0124657 A1 | 6/2005 | Christ et al. |
| 2005/0124885 A1 | 6/2005 | Abend et al. |
| 2005/0187255 A1 | 8/2005 | Lee et al. |
| 2006/0025592 A1 | 2/2006 | Stranix et al. |
| 2006/0063792 A1 | 3/2006 | Dolle et al. |
| 2006/0094658 A1 | 5/2006 | Currie et al. |
| 2006/0115424 A1 | 6/2006 | Gray |
| 2006/0128742 A1 | 6/2006 | Edwards et al. |
| 2006/0204512 A1 | 9/2006 | Krasnoperov et al. |
| 2006/0205753 A1 | 9/2006 | Israel |
| 2006/0258696 A1 | 11/2006 | Moss et al. |
| 2007/0010450 A1 | 1/2007 | Currie et al. |
| 2007/0020261 A1 | 1/2007 | Sliwkowski et al. |
| 2007/0060501 A1 | 3/2007 | Jhamandas et al. |
| 2007/0071761 A1 | 3/2007 | Seon |
| 2007/0082044 A1 | 4/2007 | Yeum |
| 2007/0099946 A1 | 5/2007 | Doshan et al. |
| 2007/0265293 A1 | 11/2007 | Boyd et al. |
| 2008/0064743 A1 | 3/2008 | Shah et al. |
| 2008/0064744 A1 | 3/2008 | Shah et al. |
| 2008/0070975 A1 | 3/2008 | Shah et al. |
| 2008/0075771 A1 | 3/2008 | Vaughn et al. |
| 2008/0103438 A1 | 5/2008 | Prais et al. |
| 2008/0194611 A1 | 8/2008 | Alverdy et al. |
| 2008/0274119 A1 | 11/2008 | Moss et al. |
| 2009/0312359 A1 | 12/2009 | Foss et al. |
| 2010/0087472 A1 | 4/2010 | Foss et al. |
| 2010/0099699 A1 | 4/2010 | Melucci |
| 2010/0105911 A1 | 4/2010 | Boyd et al. |
| 2010/0120813 A1 | 5/2010 | Bazhina et al. |
| 2010/0249169 A1 | 9/2010 | Shah et al. |
| 2010/0261744 A1 | 10/2010 | Sanghvi et al. |
| 2010/0261745 A1 | 10/2010 | Sanghvi et al. |
| 2010/0261746 A1 | 10/2010 | Sanghvi et al. |
| 2010/0267758 A1 | 10/2010 | Sanghvi et al. |
| 2010/0305323 A1 | 12/2010 | Smolenskaya et al. |
| 2010/0311781 A1 | 12/2010 | Doshan et al. |
| 2012/0059025 A1 | 3/2012 | Shah et al. |
| 2014/0228389 A1 | 8/2014 | Shah et al. |
| 2015/0025100 A1 | 1/2015 | Shah et al. |
| 2015/0290187 A1 | 10/2015 | Doshan et al. |
| 2016/0338946 A1 | 11/2016 | Shah et al. |

FOREIGN PATENT DOCUMENTS

| | | |
|---|---|---|
| AU | 758416 B2 | 3/2003 |
| AU | 2003204844 B2 | 6/2007 |
| BE | 876 968 A1 | 10/1979 |
| CA | 2 064 373 A1 | 9/1992 |
| CA | 1 315 689 C | 4/1993 |
| CA | 2293008 A1 | 7/2000 |
| CA | 2312234 | 3/2005 |
| DE | 3 780 819 T2 | 1/1993 |
| DE | 4 303 214 A1 | 8/1994 |
| DE | 196 51 551 A1 | 6/1998 |
| EP | 0 278 821 A1 | 8/1988 |
| EP | 0 289 070 A1 | 11/1988 |
| EP | 0 306 575 A1 | 3/1989 |
| EP | 0 352 361 A1 | 1/1990 |
| EP | 0 506 468 A1 | 9/1992 |
| EP | 0 643 967 A2 | 3/1995 |
| EP | 0 663 401 A1 | 7/1995 |
| EP | 0 760 661 A1 | 3/1997 |
| EP | 0880352 A2 | 12/1998 |
| EP | 0913152 A1 | 5/1999 |
| EP | 0 984 004 A2 | 3/2000 |
| EP | 1 047 726 A1 | 11/2000 |
| EP | 2368553 A1 | 9/2011 |
| ES | 2226933 T3 | 4/2005 |
| GB | 1 202 148 A | 8/1970 |
| JP | 1 068 376 | 3/1989 |
| JP | 2025427 | 1/1990 |
| JP | 2 625 457 B2 | 7/1997 |
| JP | 4-183371 B2 | 11/2008 |
| JP | 4-217924 B2 | 2/2009 |
| JP | 4-225922 B2 | 2/2009 |
| JP | 5-213763 B2 | 6/2013 |
| NZ | 222911 A | 11/1990 |
| SG | 116167 | 1/2008 |
| SG | 2005064639 | 1/2008 |
| WO | 83/03197 A1 | 9/1983 |
| WO | 88/05297 A1 | 7/1988 |
| WO | 93/20826 A1 | 10/1993 |
| WO | 94/10202 A1 | 5/1994 |
| WO | 95/31985 A2 | 11/1995 |
| WO | 96/14058 A1 | 5/1996 |
| WO | 96/23793 A1 | 8/1996 |
| WO | 97/07118 A1 | 2/1997 |
| WO | 97/29739 A2 | 8/1997 |
| WO | 97/33566 A2 | 9/1997 |
| WO | 98/25613 A2 | 6/1998 |
| WO | WO-98/35679 A1 | 8/1998 |
| WO | WO-98/49185 A1 | 11/1998 |
| WO | 99/22737 A1 | 5/1999 |
| WO | 99/36470 A1 | 7/1999 |
| WO | WO-99/37681 A2 | 7/1999 |
| WO | 99/40089 A1 | 8/1999 |
| WO | WO-00/40968 A1 | 7/2000 |
| WO | WO-00/43507 A1 | 7/2000 |
| WO | WO-00/46383 A2 | 8/2000 |
| WO | WO-00/65057 A1 | 11/2000 |
| WO | WO-01/09300 A2 | 2/2001 |
| WO | 01/13909 A2 | 3/2001 |
| WO | 01/32180 A2 | 5/2001 |
| WO | 01/37785 A2 | 5/2001 |
| WO | 01/41705 A2 | 6/2001 |
| WO | 01/42207 A2 | 6/2001 |
| WO | 01/70031 A1 | 9/2001 |
| WO | 01/85257 A2 | 11/2001 |
| WO | 02/47661 A1 | 6/2002 |
| WO | 02/47685 A2 | 6/2002 |
| WO | 02/060870 A2 | 8/2002 |
| WO | 02/098422 A1 | 12/2002 |
| WO | 03/020296 A1 | 3/2003 |
| WO | 03/032990 A2 | 4/2003 |
| WO | 03/037340 A1 | 5/2003 |
| WO | 03/077867 A2 | 9/2003 |
| WO | 2004/014291 A2 | 2/2004 |
| WO | 2004/043964 A2 | 5/2004 |
| WO | 2004/080996 A1 | 9/2004 |
| WO | 2004/091623 A1 | 10/2004 |
| WO | 2006/096626 A2 | 9/2006 |
| WO | 2006/127898 A2 | 11/2006 |
| WO | 2006/127899 A2 | 11/2006 |
| WO | 2006/132963 A2 | 12/2006 |
| WO | 2006/135650 A1 | 12/2006 |
| WO | 2007/053194 A2 | 5/2007 |
| WO | 2007/053698 A2 | 5/2007 |
| WO | 2007/131154 A2 | 11/2007 |
| WO | 2008/016704 A1 | 2/2008 |
| WO | 2008/019115 A2 | 2/2008 |
| WO | 2008/064150 A1 | 5/2008 |
| WO | 2008/064351 A2 | 5/2008 |
| WO | 2008/064353 A2 | 5/2008 |
| WO | 2008/070462 A2 | 6/2008 |
| WO | 2008/121348 A2 | 10/2008 |

(56) References Cited

FOREIGN PATENT DOCUMENTS

| WO | 2008/121860 A1 | 10/2008 |
|---|---|---|
| WO | WO-2008/121352 A2 | 10/2008 |

OTHER PUBLICATIONS

University of California, Berkley Buffer website (citing data from Ruzin, 1999, Plant Microtechnique and Microscopy), at web address: microscopy.berkeley.edu/Resources/instruction/buffers.html (1999)).*
Lysle et al., Modulation of immune status by a conditioned aversive stimulus: evidence for the involvement of endogenous opioids. Brain Behav Immun. Jun. 1992;6(2): 179-88.
Machelska et al., Selectins and integrins but not platelet-endothelial cell adhesion molecule-1 regulate opioid inhibition of inflammatory pain. Br J Pharmacol. Jun. 2004; 142(4):772-80. Epub May 24, 2004.
Mack, Paralytic ileus: response to naloxone. Br J Surg. Oct. 1989;76(10):1101.
Magazine et al., Morphine-induced conformational changes in human monocytes, granulocytes, and endothelial cells and in invertebrate immunocytes and microglia are mediated by nitric oxide. J Immunol. Jun. 15, 1996;156(12):4845-50.
Magnan et al., The binding spectrum of narcotic analgesic drugs with different agonist and antagonist properties. Naunyn Schmiedebergs Arch Pharmacol. Jun. 1982;319(3): 197-205.
Maguire et al., Pharmacological profiles of fentanyl analogs at mu, delta and kappa opiate receptors. Eur J Pharmacol. Mar. 24, 1992;213(2):219-25. Abstract Only.
Malspeis et al., Metabolic Reduction of Naltrexone I. Synthesis, Separation and Characterization of Naloxone and Maltrexone Reduction Products and Qualitative Assay of Urine and Bile Following Adminstration of Naltrexone, alpha-naltrexol, or beta-naltrexol. Chem Pathol Pharmacol. 1975;12(1):43-65.
Manara et al., Inhibition of gastrointestinal transit by morphine in rats results primarily from direct drug action on gut opioid sites. J Pharmacol Exp Ther. Jun. 1986;237(3):945-9. Abstract Only.
Manara et al., Peripheral selectivity of quaternary narcotic antagonists: relative ability to prevent gastrointestinal transit inhibition and antinociception in morphinized rats. Adv. Endog. Exog. Opioids, Poroc. Int. Narc. Res. Conf., 12th (1981): 402-4.
Manara et al., The central and peripheral influences of opioids on gastrointestinal propulsion. Annu Rev Pharmacol Toxicol. 1985;25:249-73.
Mancev et al., The immunomodulating effects of specific opioid receptor antagonists after their intracerebroventricular application. Intl J Thymol. 1999;7(12-13):589-95.
Marmor et al., Coronary artery disease and opioid use. Am J Cardiol. May 15, 2004;93(10): 1295-7.
McBride et al., delta2 opioid receptor agonist facilitates mean arterial pressure recovery after hemorrhage in conscious rats. Shock. Mar. 2005;23(3):264-8.
McCance-Katz et al., Interactions between buprenorphine and antiretrovirals. II. The protease inhibitors nelfmavir, lopinavir/ritonavir, and ritonavir. Clin Infect Dis. Dec. 15, 2006;43 Suppl 4:S235-46.
McCarthy et al., Opioids, opioid receptors, and the immune response. Drug Alcohol Depend. Apr. 1, 2001;62(2):111-23.
McCarthy et al., Preliminary studies on the use of plasma beta-endorphin in horses as an indicator of stress and pain. J Equine Vet Sci. 1993;13(4):216-9.
MQuay et al., Opioid problems and morphine metabolism and excretion. http://www.medicine.ox.ac.uk/bandolier/booth/painpag/wisdom/c14.html. Last accessed Feb. 8, 2010. 24 pages.
McQuay, Opioid use in chronic pain. Acta Anaesthesiol Scand. Jan. 1997;41(1 Pt 2): 175-83.
Mellon et al., Evidence for central opioid receptors in the immunomodulatory effects of morphine: review of potential mechanism(s) of action. J Neuroimmunol. Mar. 15, 1998;83(1-2): 19-28.

Melzig et al., Stimulation of endothelial angiotensin-converting enzyme by morphine via non-opioid receptor mediated processes. Pharmazie. Sep. 1998;53(9):634-7.
Mickley et al., Quaternary naltrexone reverses morphine-induced behaviors. Physiol Behav. Aug. 1985;35(2):249-53.
Miedema et al., Methods for decreasing postoperative gut dysmotility. Lancet Oncol. Jun. 2003;4(6):365-72.
Misra et al., Intravenous kinetics and metabolism of [15,16-3H]naltrexonium methiodide in the rat. J Pharm Pharmacol. Mar. 1987;39(3):225-7.
Miyagi et al., Morphine induces gene expression of CCR5 in human CEMx174 lymphocytes. J Biol Chem. Oct. 6, 2000;275(40):31305-10.
Moerman et al., Evaluation of methylnaltrexone for the reduction of postoperative vomiting and nausea incidences. Acta Anaesthesiol Belg. 1995;46(3-4):127-32.
Moss, et al., Selective postoperative inhibition of gastrointestinal opioid receptors. N. Engl. J. Med. 2002;346(6):455.
Moss et al., Methylnaltrexone prevents morphine-induced CCR5 receptor expression. Anesthesiology. 2003;99. Abstract A-961.
Moss et al., Opioid-induced changes in pulmonary barrier integrity may explain heroid-induced pulmonary edema. American Society of Anesthesiologists presentation, Oct. 17, 2007 in San Francisco, CA. Abstract A 1980.
Moss et al., Pain relief without side effects: peripheral opiate antagonists. 33rd ASA Refresher Courses in Anesthesiology, Philadelphia, Lippincott Williams * Wilkins, Schwartz, A.J. editor. 2006;33: 175-86.
Mucha, Is the motivational effect of opiate withdrawal reflected by common somatic indices of precipitated withdrawal? A place conditioning study in the rat. Brain Res. Aug. 25, 1987;418(2):214-20.
Mucha, Taste aversion involving central opioid antagonism is potentiated in morphine-dependent rats. Life Sci. 1989;45(8):671-8.
Murphy et al., Pharmaconkinetic of epidural administered methylnaltrexone a novel peripheral opioid anatagonist. American Society of Anesthesiologists, 1999 annual meeting. Dallas, Texas, USA. Oct. 9-13, 1999. Anesthesiology. Sep. 1999;91(3A Suppl):A349.
Murphy et al., Opioid antagonist modulation of ischaemia-induced ventricular arrhythmias: a peripheral mechanism. J Cardiovasc Pharmacol. Jan. 1999;33(1):122-5.
Murphy et al., Opioid-induced delay in gastric emptying: a peripheral mechanism in humans. Anesthesiology. Oct. 1997;87(4):765-70.
Murphy et al., Pharmacokinetic profile of epidurally administered methylnaltrexone, a novel peripheral opioid antagonist in a rabbit model. Br J Anaesth. Jan. 2001;86(1):120-2.
Nair et al., Morphine Modulates the Expression of Chemokines and their Receptors by Peripheral Blood Mononuclear Cells (PBMC) from Normal Donors. J Allergy Clin Immunol. 1998: 101(1):S57. Abstract 244.
Naranjo et al., Evidence for a central but not adrenal, opioid mediation in hypertension induced by brief isolation in the rat. Life Sci. May 26, 1986;38(21):1923-30.
Nelson, Morphine modulation of the contact hypersensitivity response: A pharmacological and immunological characterization. University of North Carolina at Chapel Hill. Dissertation Abstracts International. 2001;62/03-B:1635. 94 pages. Abstract Only.
Nelson et al., Involvement of central mu- but not delta- or kappa-opioid receptors in immunomodulation. Brain Behav Immun. Sep. 2000; 14(3): 170-84.
Nemeth-Lefkowitz et al., Hematological and Immunological Effects of Methadone Administration in Mice. Research Communication in Substances of Abuse. 1980; 1 (2): 177-83.
Neumann et al., Plasma morphine concentrations during chronic oral administration in patients with cancer pain. Pain. Jul. 1982; 13(3):247-52.
Nielsen et al., Glycolamide Esters as Biolabile Prodrugs of Carboxylic Acid Agents: Synthesis, Stability, Bioconversion, and Physicochemical Properties. J Pharma Sci. 1988;77:285-98.

(56) References Cited

OTHER PUBLICATIONS

Niemegeers et al., Difenoxine (R 15403), the active metabolite of diphenoxylate (R 1132). 2. Difneozine, a potent, orally active and safe antidiarrheal agent in rats. Arzneimittelforschung. Mar. 1972;22(3):516-8.

Novick et al., Natural killer cell activity and lymphocyte subsets in parenteral heroin abusers and long-term methadone maintenance patients. J Pharmacol Exp Ther. Aug. 1989;250(2):606-10.

Odio et al., Central but not peripheral opiate receptor blockade prolonged pituitary-adrenal responses to stress. Pharmacol Biochem Behav. Apr. 1990;35(4):963-9.

O'Keefe et al., Bowel Disorders Impair Functional Status and Quality of Life in the Elderly: A Population-Based Study. J Gerontol. 1995;50:184-89.

Osinski et al., Determination of methylnaltrexone in clinical samples by solid-phase extraction and high-performance liquid chromatography for a pharmacokinetics study. J Chromatogr B Analyt Technol Biomed Life Sci. Nov. 25, 2002;780(2):251-9.

Papapetropoulos et al., Nitric oxide synthase inhibitors attenuate transforming-growth-factor-beta 1-stimulated capillary organization in vitro. Am J Pathol. May 1997;150(5):1835-44.

Pappagallo, Incidence, prevalence, and management of opioid bowel dysfunction. Am J Surg. Nov. 2001; 182(5A Suppl): 11S-18S.

Pasi et al., Angiogenesis: modulation with opioids. Gen Pharmacol. 1991;22(6):1077-9.

Schmidhammer et al. "5-Methylnaloxone and 5-methylnaltrexone: Synthesis and Pharmaceucal Evaluation." Helvetica Chimica Acta, 1990, 73(7), 1986-1990.

Yuan et al. "Effects of methylnaltrexone on morphine-induced inhibition of contraction in isolated guinea-pig ileum and human intestine." Eur J Pharmacol., 1995,276(1-2), 107-111.

Wentland et al., Synthesis and opioid receptor binding properties of a highly potent 4-hydroxy analogue of naltrexone. Bioorg Med Chem Lett. Apr. 15, 2005;15(8):2107-10.

Whistler et al., Functional dissociation of mu opioid receptor signaling and endocytosis: implications for the biology of opiate tolerance and addiction. Neuron. Aug. 1999;23(4):737-46.

Willett et al., Direct evidence that the VEGF-specific antibody bevacizumab has antivascular effects in human rectal cancer. Nat Med. Feb. 2004; 10(2): 145-7. Epub Jan. 25, 2004.

Willette, et al., Evidence for anticholinergic effects of naltrexone methylbromide. Res Comm Subst Abuse. 1983;4(4):325-37.

Wilmore et al., Can we minimize the effects of opioids on the bowel and still achieve adequate pain control? Am J Surg. Nov. 2001; 182(5A Suppl): 1S-2S.

Wingo et al., Cancer statistics, 1995. CA Cancer J Clin. Jan.-Feb. 1995;45(1):8-30.

Witkin et al., Pharmacology of 2-amino-indane hydrochloride (Su-8629): a potent non-narcotic analgesic. J Pharmacol Exp Ther. Sep. 1961;133:400-8. Abstract Only.

Wittert et al., Tissue distribution of opioid receptor gene expression in the rat. Biochem Biophys Res Commun. Jan. 26, 1996;218(3):877-81.

Wolff et al., Alvimopan, a novel, peripherally acting mu opioid antagonist: results of a multicenter, randomized, double-blind, placebo-controlled, phase III trial of major abdominal surgery and postoperative ileus. Ann Surg. Oct. 2004;240(4):728-34; discussion 734-5.

Wybran et al., Suggestive evidence for receptors for morphine and methionine-enkephalin on normal human blood T lymphocytes. J Immunol. Sep. 1979; 123(3): 1068-70.

Yamamoto et al., Inhibition of stress-stimulated colonic propulsion by alpha 2-adrenoceptor antagonists in rats. Neurogastroenterol Motil. Dec. 1998;10(6):523-32. Abstract Only.

Yeh et al., Stability of morphine in aqueous solution. Am J Hosp Pharmacy. 1960; 17(2): 101-103.

Yoshida et al., Effect of surgical stress on endogenous morphine and cytokine levels in the plasma after laparoscopoic or open cholecystectomy. Surg Endosc. Feb. 2000; 14(2): 137-40.

Yuan et al., Antagonism of chronic opioid-induce gut effects. Anesth Analg. 2000;90:S1-523. Abstract S479.

Yuan et al., Antagonism of gastrointestinal opioid effects. Reg Anesth Pain Med. Nov.-Dec. 2000;25(6):639-42.

Yuan et al., Clinical status of methylnaltrexone, a new agent to prevent and manage opioid-induced side effects. J Support Oncol. Mar.-Apr. 2004;2(2): 111-7; discussion 119-22.

Yuan et al., Dose-related effects of oral acetaminophen on cold-induced pain: a double-blind, randomized, placebo-controlled trial. Clin Pharmacol Ther. Mar. 1998;63(3):379-83.

Yuan et al., Effects of enteric-coated methylnaltrexone in preventing opioid-induced delay in oral-cecal transit time. Clin Pharmacol Ther. Apr. 2000;67( 4):398-404.

Yuan et al., Effects of intravenous methylnaltrexone on opioid-induced gut motility and transit time changes in subjects receiving chronic methadone therapy: a pilot study. Pain. Dec. 1999;83(3):631-5.

Yuan et al., Effects of low-dose morphine on gastric emptying in healthy volunteers. J Clin Pharmacol. Nov. 1998;38(11):1017-20.

Yuan et al., Effects of methylnaltrexone on chronic opioid induced gut motility and transit time changes. Br J Anaesth. 1998;81(1):94. Abstract Only.

Yuan et al., Effects of methylnaltrexone on chronic opioid-induced gut motility and transit time changes. University of Leicester—Abstracts from the Eighth International Symposium on Pain, Anaesthesia and Endocrinology. Sep. 18-19, 1997.

Yuan et al., Effects of methylnaltrexone on morphine-induced inhibition of contractions in isolated guinea-pig and human intestine. Anesthesiology. Sep. 1995; 83(3A). Abstract A358.

Yuan et al., Effects of methylnaltrexone on morphine-induced inhibition of contraction in isolated guinea-pig ileum and human intestine. Eur J Pharmacol. Mar. 24, 1995;276(1-2): 107-11.

Yuan et al., Effects of subcutaneous methylnaltrexone on morphine-induced peripherally mediated side effects: a double-blind randomized placebo-controlled trial. J Pharmacol Exp Ther. Jan. 2002;300(1):118-23.

Yuan et al., Efficacy of orally administered methylnaltrexone in decreasing subjective effects after intravenous morphine. Drug Alcohol Depend. Oct. 1, 1998;52(2):161-5.

Yuan et al., Gastric effects of methylnaltrexone on mu, kappa, and delta opioid agonists induced brainstem unitary responses. Neuropharmacology. Mar. 1999; 38(3):425-32.

Yuan et al., Gastric effects of mu-, delta- and kappa-opioid receptor agonists on brainstem unitary responses in the neonatal rat. Eur J Pharmacol. Oct. 24, 1996;314(1-2):27-32.

Yuan et al., Gut and brain effects of American ginseng root on brainstem neuronal activities in rats. Amer J Chin Med. 1998; 26: 47-55.

Yuan et al., Gut motility and transit changes in patients receiving long-term methadone maintenance. J Clin Pharmacol. Oct. 1998;38(10):931-5.

Yuan et al., Methylnaltrexone, a novel peripheral opioid receptor antagonist for the treatment of opioid side effects. Expert Opin Investig Drugs. May 2006;15(5):541-52.

Yuan et al., Methylnaltrexone (MNTX) for chronic opioid-induced constipation. 2002 ASCO Annual Meeting. Proc Am Soc Clin Oncol. 2002;21:376a. Abstract 1501.

Yuan et al., Methylnaltrexone (MNTX) reverses chronic opioid constipation: a double-blind, randomized, placebo-controlled trial. Anesthesiology. Sep. 1999; 91 (3A). Abstract A973.

Yuan et al., Methylnaltrexone changes gut motility and transit time in chronic methadone-maintained subjects. Anesth Analg. 1999;88: SI-424. Abstract S404.

Yuan et al., Methylnaltrexone effects on morphine-induced inhibition in isolated guinea-pig and human intestine. Clin Pharm & Therapeut. Feb. 1995;57:138. Abstract PI-11.

Yuan et al., Methylnaltrexone for reversal of constipation due to chronic methadone use: a randomized controlled trial. JAMA. Jan. 19, 2000;283(3):367-72.

Yuan et al., Methylnaltrexone prevents morphine-induced delay in oral-cecal transit time without affecting analgesia: a double-blind randomized placebo-controlled trial. Clin Pharmacol Ther. Apr. 1996;59(4):469-75.

(56) References Cited

OTHER PUBLICATIONS

Yuan et al., Methylnaltrexone prevents morphine-induced kaolin intake in the rat. Anesthesiology. 2003;99. Abstract A-922.
Yuan et al., Methylnaltrexone reduces oral-cecal transit time in humans. Dig Dis Week Abstr. 2003 :A-578. Abstract T1840.
Yuan et al., Methylnaltrexone reverses morphine-induced changes in gastrointestinal motility: a clinical study. Anesthesiology Sep. 1995; 83(3A): Abstract A360.
Yuan et al., Methylnaltrexone: investigation of clinical applications. Drug Develop Res. 2000;50(2): 133-41.
Yuan et al., Opioid analgesia without gut side effects: effects of methylnaltrexone as a novel peripheral opioid antagonist. Assoc Univ Anesth Abst. 2003: PD2.
Yuan et al., Oral methylnaltrexone for opioid-induced constipation. JAMA. Sep. 20, 2000;284(11): 1383-4.
Yuan et al., Oral methylnaltrexone reverses chronic opioid-induced constipation. Anesthesiology. Sep. 2000;93(3A). Abstract A-872.
Yuan et al., Oral methylnaltrexone reverses morphine-induced changes in gastrointestinal motility. Anesthesiology. Sep. 1995;85(3A). Abstract A335.
Yuan et al., Pain control without side effects: clinical studies on methylnaltrexone as a novel peripheral opioid antagonist. 7th America—Japan Anesth Congr. Yamanashi, Japan. 2002:41.
Yuan et al., Pharmacokinetics of intravenous vs. oral methylnaltrexone: evidence for direct gut effects. Anesth Analg. 2001;92: S1-363. Abstract S274.
Yuan et al., Safety and tolerance of oral methylnaltrexone in healthy volunteers. Anesth Analg. 1997;84:S1-599. Abstract S574.
Yuan et al., Subcutaneous methylnaltrexone prevents morphine-induced delay in gut transit time: a clinical trial. Anesthesiology. 2001;95. Abstract A-963.
Yuan et al., The safety and efficacy of oral methylnaltrexone in preventing morphine-induced delay in oral-cecal transit time. Clin Pharmacol Ther. Apr. 1997;61(4):467-75.
Patel et al., COX-2 and iNOS in opioid-induced delayed cardioprotection in the intact rat. Life Sci. May 28, 2004;75(2):129-40.
Paulson et al., Alvimopan: an oral, peripherally acting, mu-opioid receptor antagonist for the treatment of opioid-induced bowel dysfunction—a 21-day treatment—randomized clinical trial. J Pain. Mar. 2005;6(3): 184-92.
Peart et al., Opioid-induced preconditioning: recent advances and future perspectives. Vascul Pharmacol. Apr.-May 2005;42(5-6):211-8. Epub Mar. 17, 2005.
Peeters et al., The motilin antagonist ANQ-11125 blocks motilide-induced contractions in vitro in the rabbit. Biochem Biophys Res Commun. Jan. 28, 1994;198(2):411-6. Abstract Only.
Peterson et al., Morphine promotes the growth of HIV-1 in human peripheral blood mononuclear cell cocultures. AIDS. Sep. 1990;4(9):869-73.
Pham et al., Drugs of Abuse: Chemistry, Pharmacology, Immunology and AIDS; National Institute of Drug Research 96: Monograph Series. U.S. Department of Health and Human Services; 1990. 243 pages.
Polak et al., Enkephalin-like immunoreactivity in the human gastrointestinal tract. Lancet. May 7, 1977;1(8019):972-4.
Polakiewicz et al., mu-Opioid receptor activates signaling pathways implicated in cell survival and translational control. J Biol Chem. Sep. 1998;273(36):23534-41.
Poonawala et al., Opioids heal ischemic wounds in the rat. Wound Repair Regen. Mar.-Apr. 2005; 13(2): 165-74.
Powell et al., Paradoxical effects of the opioid antagonist naltrexone on morphine analgesia, tolerance, and reward in rats. J Pharmacol Exp Ther. Feb. 2002;300(2):588-96.
Pugsley et al., Cardiovascular actions of the kappa-agonist, U-50,488H, in the absence and presence of opioid receptor blockade. Br J Pharmacol. Mar. 1992; 105(3):521-6.
Quang-Contagrel et al., Long-term methadone treatment: effect on CD4+ lymphocyte counts and HIV-1 plasma RNA level in patients with HIV infection. Eur J Pain. 2001;5(4):415-20.

Quock, et al, Microwave facilitation of methylnaltrexone antagonism of morphine-induced analgesia in mice. J Bioelect. 1986;5(1):35-46.
Quock et al., Narcotic antagonist-induced hypotension in the spontaneously hypertensive rat. Life Sci. Sep. 2, 1985;37(9):819-26.
Quock et al., Narcotic antagonist potentiation of apomorphine drug effect: a stereospecific, centrally mediated drug action. Prog Neuropsychopharmacol Biol Psychiatry. 1985;9(3):239-43.
Radulovic et al., Opioid receptor-mediated suppression of humoral immune response in vivo and in vitro: involvement of kappa opioid receptors. J Neuroimmunol. Mar. 1995;57(1-2):55-62.
Ramabadran, Effects of N-methylnaloxone and N-methylnaltrexone on nociception and precipitated abstinence in mice. Life Sci. Sep. 20-27, 1982;31(12-13): 1253-6.
Read et al., Interpretation of the breath hydrogen profile obtained after ingesting a solid meal containing unabsorbable carbohydrate. Gut. Aug. 1985;26(8):834-42.
Reisine et al., Opioid Analgesics and Antagonists. In: Goodman & Goodman's The Pharmacological Basis of Therapeutics. 9th Ed. 1996:521-55.
Remington's: The science and practice of pharmacy (1985), pp. 187-189, 257.
Remington's: The science and practice of pharmacy (1985), pp. 1102, 1106-1107, 1493, 1523.
Resnick et al., Delayed gastric emptying and postoperative ileus after nongastric abdominal surgery: part I. Am J Gastroenterol. May 1997;92(5):751-62.
Resnick et al., Delayed gastric emptying and postoperative ileus after nongastric abdominal surgery: part II. Am J Gastroenterol. Jun. 1997;92(6):934-40.
Risdahl et al., Opiates and infection. J Neuroimmunol. Mar. 15, 1998;83(1-2):4-18.
Rivière et al., Fedotozine reverses ileus induced by surgery or peritonitis: action at peripheral kappa-opioid receptors. Gastroenterology. Mar. 1993; 1 04(3):724-31.
Robinson et al., Oral naloxone in opioid-associated constipation. Lancet. Aug. 31, 1991;338(8766):581-2.
Roger et al., Colonic motor responses in the pony: relevance of colonic stimulation by opiate antagonists. Am J Vet Res. Jan. 1985;46(1):31-5.
Roy et al., Morphine modulates NF kappa B activation in macrophages. Biochem Biophys Res Commun. Apr. 17, 1998;245(2):392-6.
Russell et al., Antagonism of gut, but not central effects of morphine with quaternary narcotic antagonists. Eur J Pharmacol. Mar. 12, 1982;78(3):255-61.
Sachs et al., Peripheral analgesic blockade of hypernociception: activation of arginine/NO/cGMP/protein kinase G/ATP-sensitive K+ channel pathway. Proc Natl Acad Sci U S A. Mar. 9, 2004;101(10):3680-5. Epub Feb. 27, 2004.
Saffran et al., A new approach to the oral administration of insulin and other peptide drugs. Science. Sep. 5, 1986;233(4768):1081-4. Abstract Only.
Sakurada et al., Differential antagonism of endomorphin-1 and endomorphin-2 supraspinal antinociception by naloxonazine and 3-methylnaltrexone. Peptides. May 2002;23(5):895-901.
Sandner-Keisling et al., Pharmacology of opioid inhibition to noxious uterine cervical distension. Anesthesiology. Oct. 2002;97(4):966-71.
Sawhney et al., Bioerodible Hydrogels Based on Photopolymerized Poly(ethylene glycol)-co-poly(alpha-hydroxy acid) Diacrylate Macromers. Macromolecules. 1993;26:581-87.
Schaefer et al., Effects of opioid antagonists and their quaternary derivatives on locomotor activity and fixed ratio responding for brain self-stimulation in rats. Pharmacol Biochem Behav. Nov. 1985;23(5):797-802.
Schang et al., Beneficial effects of naloxone in a patient with intestinal pseudoobstruction. Am J Gastroenterol. Jun. 1985;80(6):407-11.
Schang et al., How does morphine work on colonic motility? An electromyographic study in the human left and sigmoid colon. Life Sci. Feb. 24, 1986;38(8):671-6.

(56) References Cited

OTHER PUBLICATIONS

Schiller et al., Studies of the mechanism of the antidiarrheal effect of codeine. J Clin Invest. Nov. 1982;70(5):999-1008.
Schmidhammer, et al., Synthesis and biological evaluation of 14-alkoxymorphinans. Part 91. 14-O-ethyl-5-methylnaltrexone, an opioid antagonist with unusual selectivity. Helv Chim Acta. 1993; (1):476-80.
Schmidhammer, et al., Synthesis and biological evaluation of 14-alkoxymorphinans. Part 101. 14-O-methyl derivatives of 5-methylnalthrexone and 5-methylnaloxone. Helv Chim Acta. 1994; 77(6): 1585-9.
Schmidt et al., Alvimopan* (ADL 8-2698) is a novel peripheral opioid antagonist. Am J Surg. Nov. 2001;182(5A Suppl):27S-38S.
Scholz, Managing constipation that's opioid-induced. 2000; 63(6): 103.
Schreier et al., Central regulation of intestinal function: morphine withdrawal diarrhea. Proc West Pharmacol Soc. 1982;25:151-4.
Schubert-Zsilavecz et al., [Das reizdarmsyndrom] The irritable bowel syndrome. Deutsche apotheker zeitung. Aug. 22, 2002; 142(34): 40-9. German.
Schug et al., A long-term survey of morphine in cancer pain patients. J Pain Symptom Manage. Jul. 1992;7(5):259-66. Abstract Only.
Schuller et al., M6G, but not morphine, inhibits GI transit in mu opioid receptor deficient mice. Society of Neuroscience Abstracts. 1998;24:524. Abstract 210.7.
Sezen et al., Renal excretory responses produced by the delta opioid agonist, BW373U86, in conscious rats. J Pharmacol Exp Ther. Oct. 1998;287(1):238-45.
Shahbazian et al., Involvement of mu- and kappa-, but not delta-, opioid receptors in the peristaltic motor depression caused by endogenous and exogenous opioids in the guinea-pig intestine. Br J Pharmacol. Feb. 2002; 135(3):741-50.
Shavit et al., Effects of a single administration of morphine or footshock stress on natural killer cell cytotoxicity. Brain Behav Immun. Dec. 1987;1(4):318-28.
Shi et al., Cardioprotective effects of morphine on rat heart suffering from ischemia and reperfusion. Chin Med J (Engl). Jul. 2003; 116(7): 1059-62.
Written Opinion for SG 200506463-9 mailed May 4, 2006 (P0453.70 115SG00).
International Search Report and Written Opinion for PCT/US2004/010997 mailed Aug. 31, 2004 (P0453.70115WO00).
International Preliminary Report on Patentability for PCT/US2004/010997 mailed Oct. 27, 2005 (P0453.70115WO00).
Office Action, mailed Oct. 2, 2008, for U.S. Appl. No. 10/821,811 (P0453.70115US01).
Office Action, mailed Mar. 12, 2009, for U.S. Appl. No. 10/821,811 (P0453.70115US01).
Office Action, mailed Dec. 10, 2010, for U.S. Appl. No. 12/639,862 (P0453.70115US03).
[No Author Listed] Endogenous opioids. http://opioids.com/opiates.html 3 pages.
[No Author Listed] Extracolonic Motility Abnormalities. Persistence of Abdominal Symptoms after Successful Surgery from Southern Medical Journal. 2002;95(9); 1042-1046. http://www.medscape.com/viewarticle/442893_4, 2 pages.
[No Author Listed] Pathophysiology. Medscape General Medicine. 2005;7(3): 17. http://www.medscape.com/viewarticle/506798_5, 3 pages.
[No Author Listed] Methylnaltrexone: MNTX. Drugs R D. 2006;7(6):374-8.
[No Author Listed] Oncology. 1996; 10(12): 1880.
[No Author Listed] Pain management; cancer-pain remedy wins orphan drug status. Cancer Biotechnology Weekly. Aug. 12, 1996; 2 pages.
[No Author Listed] Progenics achieves enrollment target in pivotal phase 3 clinical trial of methylnaltrexone for opioid-induced constipation. Press Release. Progenics Pharmaceuticals, Inc. Dec. 3, 2004.
[No Author Listed] Progenics announces positive top-line results from pivotal phase 3 clinical trial of MNTX in opioid-induced constipation. Press Release. Progenics Pharmaceuticals, Inc. Mar. 10, 2005.
[No Author Listed] Progenics initiates second phase 3 clinical trial of methylnaltrexone in opioid-induced constipation. Press Release. Progenics Pharmaceuticals, Inc. Jan. 13, 2004.
[No Author Listed] Remington's Pharmaceutical Sciences. 15th Edition. 1995: 201-02, 273-74, 1466, 1614-5.
[No Author Listed] Remington's Pharmaceutical Sciences. 15th Edition. 1995: 278-79, 283-84.
[No Author Listed] The Merck Manual. 17th edition. 1999: 312-315.
Akinbami et al., Effect of a peripheral and a central acting opioid antagonist on the testicular response to stress in rats. Neuroendocrinology. Apr. 1994;59(4):343-8.
Altier et al., Opioid receptors in the ventral tegmental area contribute to stress-induced analgesia in the formalin test for tonic pain. Brain Res. Apr. 29, 1996; 718(1-2): 203-6.
Amin et al., Efficacy of methylnaltrexone versus naloxone for reversal of morphine-induced depression of hypoxic ventilatory response. Anesth Analg. Apr. 1994;78(4):701-5.
Amir et al., Endorphins in endotoxin-induced hyperglycemia in mice. Arch Toxicol Suppl. 1983;6:261-5.
Amir, Naloxone improves, and morphine exacerbates, experimental shock induced by release of endogenous histamine by compound 48/80. Brain Res. Apr. 9, 1984;297(1): 187-90.
Arendt et al., Bidirectional effects of endogenous opioid peptides on endothelin release rates in porcine aortic endothelial cell culture: mediation by delta opioid receptor and opioid receptor antagonist-insensitive mechanisms. J Pharmacol Exp Ther. Jan. 1995;272(1): 1-7.
Arerangaiah et al., Opioids induce renal abnormalities in tumor-bearing mice. Nephron Exp Nephrol. 2007;105(3): e80-9. Epub Jan. 12, 2007.
Argentieri et al., Interaction of the opiate antagonist, naltrexone methyl bromide, with the acetylcholine receptor system of the motor end-plate. Brain Res. Oct. 31, 1983; 277(2):377-9.
Armstead, Relationship among NO, the KATP channel, and opioids in hypoxic pial artery dilation. Am J Physiol. Sep. 1998;275(3 Pt 2):H988-94.
Armstrong et al., The gastrointestinal activity and peripheral selectivity of alvimopan, ADL08-0011, and naloxone in mice. May 21, 2006 DDW Presentation in Los Angeles. Clincial Phar Therap. 2005;77:74. Abstract #221957.
Attali et al., Kappa opiate agonists inhibit Ca2+ influx in rat spinal cord-dorsal root ganglion cocultures. Involvement of a GTP-binding protein. J Biol Chem. Jan. 5, 1989;264(1):347-53.
Aung et al., Methylnaltrexone prevents morphine-induced kaolin intake in the rat. Life Sci. Apr. 16, 2004;74(22):2685-91.
Aung et al., Scutellaria baicalensis decreases ritonavir-induced nausea. AIDS Res Ther. Dec. 20, 2005;2:12.
Bagnol et al., Changes in enkephalin immunoreactivity of sympathetic ganglia and digestive tract of the cat after splanchnic nerve ligation. Regul Pept. Sep. 22, 1993;47(3):259-73. Abstract Only.
Baker et al., Functional effects of systemically administered agonists and antagonists of mu, delta, and kappa opioid receptor subtypes on body temperature in mice. J Pharmacol Exp Ther. Sep. 2002;302(3): 1253-64.
Balasubramanian et al., Morphine sulfate inhibits hypoxia-induced vascular endothelial growth factor expression in endothelial cells and cardiac myocytes. J Mol Cell Cardiol. Dec. 2001;33(12):2179-87.
Baratti et al., Brain opioid peptides may participate in the reversal of pentylenetetrazol-induced amnesia. Methods Find Exp Clin Pharmacol. Sep. 1990;12(7):451-6.
Basilisco et al., Oral naloxone antagonizes loperamide-induced delay of orocecal transit. Dig Dis Sci. Aug. 1987;32(8):829-32.
Basilisco et al., Effect of loperamide and naloxone on mouth-to-caecum transit time evaluated by lactulose hydrogen breath test. Gut. Jul. 1985;26(7):700-3.
Bedingfield et al., Methylnaltrexone attenuates taste aversion conditioned by low-dose ethanol. Alcohol. Jan. 1998;15(1):51-4.

(56) References Cited

OTHER PUBLICATIONS

Belcheva et al., μ-Opioid receptor-mediated ERK activation involves calmodulin-dependent epidermal growth factor receptor transactivation. J Biol Chem. Sep. 7, 2001;276(36):33847-53. Epub Jul. 16, 2001.

Belcheva et al., μ-opioid transactivation and down-regulation of the epidermal growth factor receptor in astrocytes: implications for mitogen-activated protein kinase signaling. Mol Pharmacol. Dec. 2003;64(6):1391-401.

Bianchetti et al., Quaternary derivatives of narcotic antagonists: stereochemical requirements at the chiral nitrogen for in vitro and in vivo activity. Life Sci. 1983;33 Suppl:415-8.

Bianchi et al., Quaternary narcotic antagonists' relative ability to prevent antinociception and gastrointestinal transit inhibition in morphine-treated rats as an index of peripheral selectivity. Life Sci. May 31, 1982 ;30(22): 1875-83.

Bickel, Stimulation of colonic motility in dogs and rats by an enkephalin analogue pentapeptide. Life Sci. 1983;33 Suppl 1 :469-72.

Bigliardi et al., Different expression of mu-opiate receptor in chronic and acute wounds and the effect of beta-endorphin on transforming growth factor beta type II receptor and cytokeratin 16 expression. J Invest Dermatol. Jan. 2003; 120(1): 145-52.

Bigliardi-Qi et al., Changes of epidermal mu-opiate receptor expression and nerve endings in chronic atopic dermatitis. Dermatology. 2005;210(2):91-9.

Binder et al., Effect of the peripherally selective kappa-opioid agonist, asimadoline, on adjuvant arthritis. Br J Pharmacol. Jun. 1998;124(4):647-54.

Blank et al., Central, stereoselective receptors mediate the acute effects of opiate antagonists on luteinizing hormone secretion. Life Sci. Oct. 27, 1986;39(17): 1493-99.

Blebea et al., Differential effects of vascular growth factors on arterial and venous angiogenesis. J Vasc Surg. Mar. 2002;35(3):532-8.

Blebea et al., Opioid growth factor modulates angiogenesis. J Vasc Surg. Aug. 2000;32(2):364-73.

Bond et al., Investigation of small bowel transit time in man utilizing pulmonary hydrogen (H2) measurements. J Lab Clin Med. Apr. 1975;85(4):546-55. Abstract Only.

Yuan et al., Tolerability, gut effects, and pharmacokinetics of methylnaltrexone following repeated intravenous administration in humans. J Clin Pharmacol. May 2005;45(5):538-46.

Zagon et al., Opioids and differentiation in human cancer cells. Neuropeptides. Oct. 2005;39(S):495-505. Epub Sep. 15, 2005.

Zagon et al., Opioids and the apoptotic pathway in human cancer cells. Neuropeptides. Apr. 2003;37(2):79-88.

Zagon et al., Opioid antagonists inhibit the growth of metastatic murine neuroblastoma. Cancer Lett. Nov. 1983;21(1):89-94.

Zagon et al., Opioid growth factor regulates the cell cycle of human neoplasias. Int J Oncol. Nov. 2000; 17(5):1053-61.

Zhang et al., Dynorphin A as a potential endogenous ligand for four members of the opioid receptor gene family. J Pharmacol Exp Ther. Jul. 1998;286(1):136-41.

Zhang et al., Effect of the endogenous kappa opioid agonist dynorphin A(1-17) on cocaine-evoked increases in striatal dopamine levels and cocaine-induced place preference in C57BL/6J mice. Psychopharmacology (Berl). Apr. 2004; 172(4):422-9. Epub Jan. 8, 2004.

Zimmerman et al., Discovery of a potent, peripherally selective trans-3,4-dimethyl-4-(3-hydroxyphenyl) piperidine opioid antagonist for the treatment of gastrointestinal motility disorders. J Med Chem. Jul. 22, 1994, 37(15):2262-5.

Office Action, mailed Jan. 26, 2009, for U.S. Appl. No. 11/890,034.

Office Action, mailed Oct. 23, 2009, for U.S. Appl. No. 11/890,034.

Bonn, Morphine stimulates tumour growth. Lancet Oncol. Sep. 2002;3(9):520.

Boonstra et al., Engineering novel biocatalytic routes for production of semisynthetic opiate drugs. Biomol Eng. Sep. 2001:18(2):41-7.

Bös et al., A Short and Efficient Synthesis of C-Nor-Dihydrocodeinone—The Antipode of Goto's Sinomenilone. Heterocycles. 1983;20(6): 1077-81.

Bowen et al., Antagonism of the antinociceptive and discriminative stimulus effects of heroin and morphine by 3-methoxynaltrexone and naltrexone in rhesus monkeys. J Pharmacol Exp Ther. Jul. 2002;302( 1 ):264-73.

Bowen et al., College on Problems of Drug Dependence 64th Annual Scientific Meeting. Jun. 8-13, 2002. Quebec City, Quebec, Canada. Abstracts. Drug Alcohol Depend. May 1, 2002 ;66 Suppl 1:S1-220. Abstract No. 65.

Breitbart et al., Control of non-pain symptoms in HIV/AIDS. J Back Musculoskelet Rehabil. 1997;8(3):243-46.

Brix-Christensen et al., Endogenous morphine is produced in response to cardiopulmonary bypass in neonatal pigs. Acta Anaesthesiol Scand. Nov. 2000;44(10): 1204-8.

Brix-Christensen et al., Endogenous morphine levels increase following cardiac surgery as part of the anti-inflammatory response? Int J Cardiol. Dec. 19, 1997;62(3):191-7.

Brondsted et al., Hydrogels for site-specific drug delivery to the colon: in vitro and in vivo degradation. Pharm Res. Dec. 1992;9(12):1540-5. Abstract Only.

Brown et al., Opiate antagonists: central sites of action in suppressing water intake of the rat. Brain Res. Sep. 28, 1981;221 (2):432-6.

Brown et al., Reversal of morphine-induced catalepsy in the rat by narcotic antagonists and their quaternary derivatives. Neuropharmacology. Mar. 1983;22(3):317-21.

Brown et al., Techniques for mechanical stimulation of cells in vitro: a review. J Biomech. Jan. 2000;33(1 ):3-14.

Brown et al., The use of quaternary narcotic antagonists in opiate research. Neuropharmacology. Mar. 1985;24(3):181-91.

Bruce et al., Microbial degradation of the morphine alkaloids: identification of morphine as an intermediate in the metabolism of morphine by Pseudomonas putida M10. Arch Microbiol. 1990;154(5):465-70.

Bruley-Des-Varannes et al., Cholécystokine et ses antagonistes: effets sur la motricité digestive. Gastroenterol Clin Biol. 1991;15:744-57. French.

Bundgaard et al., (C) Means to Enhance Penetration. (1) Prodrugs as a means to improve the delivery of peptide drugs. J Drug Delivery Rev. 1992;8:1-38.

Burkhart et al., Metkephamid (Tyr-D-Ala-Gly-Phe-N(Me)Met-NH2), a Potent Opioid Peptide: Receptor Binding and Analgesic Properties. Peptides. 1982;3:869-71.

Caballero-Hernandez et al, Potentiation of rat lymphocyte proliferation by novel non-peptidic synthetic opioids. Int Immunopharmacol. Jul. 2005;5(7-8):1271-8. Epub Apr. 12, 2005.

Cadet et al., Differential expression of the human mu opiate receptor from different primary vascular endothelial cells. Med Sci Monit. Oct. 2004; 10(10):BR351-5. Epub Sep. 23, 2004.

Cadet et al., Molecular identification and functional expression of mu 3, a novel alternative spliced variant of the human mu opiate receptor gene. J Immunol. May 15, 2003;170(10):5118-23.

Calcagnetti et al., Quaternary naltrexone reveals the central mediation of conditional opioid analgesia. Pharmacol Biochem Behav. Jul. 1987;27(3):529-31.

Cao et al., Cardioprotection of interleukin-2 is mediated via kappa-opioid receptors. J Pharmacol Exp Ther. May 2004;309(2):560-7. Epub Jan. 27, 2004.

Carmeliet et al., Angiogenesis in cancer and other diseases. Nature. Sep. 14, 2000;407(6801):249-57.

Carr et al., Naltrexone antagonizes the analgesic and immunosuppressive effects of morphine in mice. J Pharmacol Exp Ther. May 1994;269(2):693-8.

Chang et al., An antiabsorptive basis for precipitated withdrawal diarrhea in morphine-dependent rats. J Pharmacol Exp Ther. Feb. 1984;228(2):364-9.

Chang et al., The association between opiates and cytokines in disease. Adv Exp Med Biol. 1998;437:4-6.

Chatterjie et al., Stereospecific synthesis of the 6beta-hydroxy metabolites of naltrexone and naloxone. J Med Chern. May 1975; 18(5):490-2. Abstract Only.

(56) References Cited

OTHER PUBLICATIONS

Chen et al., Morphine stimulates vascular endothelial growth factor-like signaling in mouse retinal endothelial cells. Curr Neurovasc Res. Aug. 2006;3(3): 171-80.
Choi et al., Opioid antagonists: a review of their role in palliative care, focusing on use in opioid-related constipation. J Pain Symptom Manage. Jul. 2002;24(1):71-90. Review.
Choi et al., Inhibition of chemokine-induced chemotaxis of monkey leukocytes by mu-opioid receptor agonists. In Vivo. Sep.-Oct. 1999; 13(5):389-96.
Collins et al., Peak plasma concentrations after oral morphine: a systematic review. J Pain Symptom Manage. Dec. 1998; 16(6):388-402.
Cone et al., The identification and measurement of two new metabolites of naltrexone in human urine. Res Commun Chem Pathol Pharmacol. Jun. 1978;20(3):413-33. Abstract Only.
Cozzolino et al., Acute effects of beta-endorphin on cardiovascular function in patients with mild to moderate chronic heart failure. Am Heart J. Sep. 2004; 148(3):E1-7.
Culpepper-Morgan et at., Treatment of opioid-induced constipation with oral naloxone: a pilot study. Clin Pharmacol Ther. Jul. 1992;52(1):90-5. Abstract Only.
D' Amato et al., Studies of three non-peptide cholecystokinin antagonists (devazepide, lorglumide and loxiglumide) in human isolated alimentary muscle and guinea-pig ileum. Br J Pharmacol. Feb. 1991; 102(2):391-5.
Dajani et at., Effects of E prostaglandins, diphenoxylate and morphine on intestinal motility in vivo. Eur J Pharmacol. Nov. 1975;34(1):105-13. Abstract Only.
Dajani et al., The pharmacology of SC-27166: a novel antidiarrheal agent. J Pharmacol Exp Ther. Dec. 1977;203(3):512-26. Abstract Only.
Daniel et al., Effects of morphine and other drugs on motility of the terminal ileum. Gastroenterology. Apr. 1959;36(4):510-23.
De Ponti et al., Methylnaltrexone Progenics. Curr Opin Investig Drugs. Apr. 2002;3(4):614-20. Review.
De Schryver et al., New developments in the treatment of irritable bowel syndrome. Scand J Gastroenterol Suppl. 2000;(232):38-42. Review.
Doherty et al., Route-dependent metabolism of morphine in the vascularly perfused rat small intestine preparation. Pharm Res. Mar. 2000; 17(3):291-8.
Dragonetti et al., Levallorphan methyl iodide (SR 58002), a potent narcotic antagonist with peripheral selectivity superior to that of other quaternary compounds. Life Sci. 1983;33 Suppl 1:477-80.
Egan et al., Prospective pharmacokinetic and pharmacodynamic validation of propofol's context sensitive T1/2. Anesthesiology. Sep. 1999;91(3A): Abstract A347.
Eisenberg, Effects of naltrexone on plasma corticosterone in opiate-naïve rats: a central action. Life Sci. Mar. 19, 1984;34(12):1185-91.
Eisenstein et al., Effect of opioids on oral *Salmonella* infection and immune function. Adv Exp Med Biol. 2001;493:169-76.
Epstein et al., Naltrexone attenuates acute cigarette smoking behavior. Pharmacol Biochem Behav. Jan. 2004;77(1):29-37.
Farooqui et al., µ opioid receptor stimulates a growth promoting and pro-angiogenic tumor microenvironment. Proc Amer Assoc Cancer Res. 2005;46. AACR Meeting Abstract, Abstract #4650.
Farooqui et al., Naloxone acts as an antagonist of estrogen receptor activity in MCF-7 cells. Mol Cancer Ther. Mar. 2006;5(3):611-20.
Farthing et al., New drugs in the management of the irritable bowel syndrome. Drugs. Jul. 1998;56(1): 11-21.
Farup et al., The Symptomatic Effect of Cisapride in Patients with Irritable Bowel Syndrome and Constipation. Scand J Gastronenerol. 1998;33:28-31.
Hofmann et al., Hypocalcemia during restraint stress in rats. Indication that gastric ulcer prophylaxis by exogenous calcium interferes with calcitonin release. Res Exp Med (Berl). May 30, 1979;175(2):159-68.

Hou et al., A mu-receptor opioid agonist induces AP-1 and NF-kappa B transcription factor activity in primary cultures of rat cortical neurons. Neurosci Lett. Jul. 19, 1996;212(3):159-62.
Howd et al., Naloxone and intestinal motility. Experientia. Oct. 15, 1978;34(10):1310-1.
Hussain et al., Improvement of the oral bioavailability of naltrexone in dogs: a prodrug approach. J Pharm Sci. May 1987;76(5):356-8.
Hussain et al., Naltrexone-3-salicylate (a prodrug of naltrexone): synthesis and pharmacokinetics in dogs. Pharm Res. Feb. 1988;5(2): 113-5.
Hutchinson et al., Assessment in the guinea-pig ileum and mouse vas deferens of benzomorphans which have strong antinociceptive activity but do not substitute for morphine in the dependent monkey. Br J Pharmacol. Dec. 1975;55(4):541-6.
Hutchinson et al., Scintigraphic measurement of ileocaecal transit in irritable bowel syndrome and chronic idiopathic constipation. Gut. Apr. 1995;36(4):585-9.
Iorio et al., Diastereoisomeric Quaternary Morphinium Salts: Synthesis, Stereochemistry and Analgesic Properties. European Journal of Medicinal Chemistry. 1984;19(1):11-16.
Iorio et al., Narcotic agonist/antagonist properties of quaternary diastereoisomers derived from oxymorphone and naloxone. Eur J Med Chem. 1984; 19(4):301-3.
Jalowiec et al., Suppression of juvenile social behavior requires antagonism of central opioid systems. Pharmacol Biochem Behav. Jul. 1989;33(3):697-700.
Jankovic et al., Quaternary naltrexone: its immunomodulatory activity and interaction with brain delta and kappa opioid receptors. Immunopharmacology. Sep.-Oct. 1994;28(2):105-12.
Jasinski, Assessment of the Abuse Potentiality of Morphinelike Drugs (Methods Used in Man). Drug Addiction J. 1997:197-258.
Jasinski, Tolerance and Dependence to opiates. Acta Anaesthesiol Scand. Jan. 1997;41(1 Pt 2):184-6.
Jenab et al., Ethanol and naloxone differentially upregulate delta opioid receptor gene expression in neuroblastoma hybrid (NG 108-15) cells. Brain Res Mol Brain Res. Nov. 1994;27(1):95-102.
Johnson et al., Stability of tacrolimus with morphine sulfate, hydromorphone hydrochloride, and ceftazidime during simulated intravenous coadministration. Am J Health Syst Pharm. Jan. 15, 1999;56(2): 164-9.
Kakeji et al., Preclinical studies of the combination of angiogenic inhibitors with cytotoxic agents. Invest New Drugs. 1997;15(1):39-48.
Kasamatsu et al., Attenuation of aortic baroreflex responses by microinjections of endomorphin-2 into the rostral ventrolateral medullary pressor area of the rat. Am J Physiol Regul Integr Comp Physiol. Jul. 2005;289(1):R59-67. Epub Feb. 17, 2005.
Kaufman et al., Role of opiate receptors in the regulation of colonic transit. Gastroenterology. Jun. 1988;94(6):1351-6.
Kehlet et al., Review of postoperative ileus. Am J Surg. Nov. 2001;182(5A Suppl):3S-10S . Review.
Keith et al., Failure of naloxone to prevent the emetic activity of apomorphine in dogs. J Vet Pharmacol Ther. Dec. 1981;4(4):31S-6.
Kim et al., Assay for methylnaltrexone in rat brain regions and serum by high-performance liquid chromatography with coulometric electrochemical detection. Chromatographia. Oct. 1989;28(7-8):359-63.
King et al., Hypothalamic-pituitary-adrenocortical (HPA) axis response and biotransformation of oral naltrexone: preliminary examination of relationship to family history of alcoholism. Neuropsychopharmacology. Jun. 2002;26(6):778-88.
Kinsman et al., Effect of naloxone on feedback regulation of small bowel transit by fat. Gastroenterology. Aug. 1984;87(2):335-7.
Knowles et al., Slow transit constipation: a model of human gut dysmotility. Review of possible aetiologies. Neurogastroenterol Motil. Apr. 2000; 12(2): 181-96.
Koblish et al., Behavioral profile of ADL 8-2698, a novel GI-restricted µ opioid receptor antagonist. Society for Neuroscience Abstracts. 2001;27(2):2407. Abstract Only.
Kobylecki et al., N-Methylnalorphine: defmition of N-allyl conformation for antagonism at the opiate receptor. J Med Chem. Nov. 1982;25(11):1278-80.

(56) References Cited

OTHER PUBLICATIONS

Koch et al., Inhibitory neuropeptides and intrinsic inhibitory innervation of descending human colon. Dig Dis Sci. Jun. 1991;36(6):712-8. Abstract Only.

Koczka, et al., Selective Quaternization of Compounds with Morphine Skeleton. Acta Chimica Academica Scien Hung. 1967;51(4):393-02.

Kodani et al., Delta-opioid receptor-induced late preconditioning is mediated by cyclooxygenase-2 in conscious rabbits. Am J Physiol Heart Circ Physiol. Nov. 2002;283(5):H1943-57.

Koob et al., Effects of opiate antagonists and their quaternary derivatives on heroin self-administration in the rat. J Pharmacol Exp Ther. May 1984;229(2):481-6.

Kosten et al., Naltrexone and morphine alter the discrimination and plasma levels of ethanol. Behav Pharmacol. Feb. 1999; 10(1): 1-13.

Kostic, CAS Abstract Document No. 127: 13345, 1997.

Kotake et al., Variations in demethylation of N-methylnaltrexone in mice, rats, dogs, and humans. Xenobiotica. Nov. 1989; 19(11): 1247-54.

Kratzel et al., An Efficient Synthesis of 14-Halogenomethyl-Substituted C-Normorphinans. Heterocycles. 1987;26(10):2703-10.

Kratzel et al., Synthesis of 5a, 11b-Propanonaphtho[1,2-e][1,2]oxazepines as Potential Opioid Analgesics. J Chem Soc Perkin 1. 1994;11:1541-43.

Kromer et al., Endogenous opioids, the enteric nervous system and gut motility. Dig Dis. 1990;8(6):361-73.

Kromer et al., The current status of opioid research on gastrointestinal motility. Life Sci. 1989;44(9):579-89.

Law et al., Agonist activation of delta-opioid receptor but not mu-opioid receptor potentiates fetal calf serum or tyrosine kinase receptor-mediated cell proliferation in a cell-line-specific manner. Mol Pharmacol. Jan. 1997;51(1):152-60.

Law et al., Properties of delta opioid receptor in neuroblastoma NS20Y: receptor activation and neuroblastoma proliferation. J Pharmacol Exp Ther. Jan. 1995;272(1):322-32.

Law et al., Regulation of opioid receptor activities. J Pharmacol Exp Ther. May 1999;289(2):607-24.

Lazar et al., Synthesis and biological activity of the phosphate and sulfate esters of naloxone and naltrexone. Eur J Med Chem. 1994;29:45-53.

Leander, A kappa opioid effect: increased urination in the rat. J Pharmacol Exp Ther. Jan. 1983 ;224(1): 89-94.

Li et al., Methadone enhances human immunodeficiency virus infection of human immune cells. J Infect Dis. Jan. 1, 2002;185(1):118-22. Epub Dec. 14, 2001.

Lim et al., Morphine preconditions Purkinje cells against cell death under in vitro simulated ischemia-reperfusion conditions. Anesthesiology. Mar. 2004; 100(3):562-8.

Linn et al., Peripherally restricted μ-opioid receptor antagonists: a review. Tech Reg Anesth Pain Manag. Jul. 2007;11(1):27-32.

Little, et al., ADL 8-2698, a GI restricted opioid antagonist, blocks the antisecretory and colorectal transit effects of morphine and loperamide. Society for Neuroscience Abstracts. 2001; 27(2):2407. Abstract Only.

Livingston et al., Postoperative ileus. Dig Dis Sci. Jan. 1990;35(1):121-32.

Lopez et al., Demonstration of long-lasting blockade of experimental ileus in rats by an opioid k-agonist. Gastroenterology. 1995;108(4):Abstract A640.

Lydon et al., Intravenous methylnaltrexone attenuates intrathecal morphine induced delayed gastric emptying in rats. ESA Free Paper Prize Competition. Eur J Anaesthesiol. Apr. 2001; 18 Suppl 21:92. Abstract A-327.

Lysle et al., Evidence for the involvement of the caudal region of the periaqueductal gray in a subset of morphine-induced alterations of immune status. J Pharmacol Exp Ther. Jun. 1996;277(3):1533-40.

Faura et al., Systematic review of factors affecting the ratios of morphine and its major metabolites. Pain. Jan. 1998;74(1):43-53.

Fecho et al., Assessment of the involvement of central nervous system and peripheral opioid receptors in the immunomodulatory effects of acute morphine treatment in rats. J Pharmacol Exp Ther. Feb. 1996;276(2):626-36.

Fernandez-Tome et al., Interaction between opioid agonists or naloxone and 5-HTP on feeding behavior in food-deprived rats. Pharmacol Biochem Behav. Feb. 1988;29(2):387-92.

Fingl, Chapter 43: Laxatives and cathartics. In Pharmacological Basis of Therapeutics. 1980: 1002-12.

Finn et al., Endocytosis of the mu opioid receptor reduces tolerance and a cellular hallmark of opiate withdrawal. Neuron. Dec. 6, 2001;32(5):829-39.

Flores et al., Mechanisms of morphine-induced immunosuppression: effect of acute morphine administration on lymphocyte trafficking. J Pharmacol Exp Ther. Mar. 1995;272(3): 1246-51.

Foss, A review of the potential role of methylnaltrexone in opioid bowel dysfunction. Am J Surg. Nov. 2001; 182(5A Suppl): 19S-26S.

Foss et al., Alvimopan (Entereg™), a novel opioid antagonist, achieves active systemic concentrations. Amer Soc Clin Pharma Ther. 2005:74. Abstract P11-90.

Foss et al., Dose-related antagonism of the emetic effect of morphine by methylnaltrexone in dogs. J Clin Pharmacol. Aug. 1993;33(8):747-51.

Foss et al., Effects of methylnaltrexone on morphine-induced cough suppression in guinea pigs. Life Sci. 1996;59(15):PL235-8.

Foss et al., Enteric-coated methylnaltrexone prevents opioid-induced oral-cecal transit delay in humans. Anesth Analg. 2000;90. Abstract S409.

Foss et al., Methylnaltrexone does not antagonize the analgesic effect of morphine: a clinical study. 1995 Annual scientific meeting of the American Society of Anesthesiologists. Atlanta, Georgia, Oct. 21-25, 1995. Abstracts. Anesthesiology. Sep. 1995;83(3A Suppl):A361.

Foss et al., Methylnaltrexone reduces morphine-induced postoperative emesis by 30%. Anesth Analg. 1994;78:S119.

Foss et al., Prevention of apomorphine- or cisplatin-induced emesis in the dog by a combination of methylnaltrexone and morphine. Cancer Chemother Pharmacol. 1998;42(4):287-91.

Foss et al., Safety and tolerance of methylnaltrexone in healthy humans: a randomized, placebo-controlled intravenous, ascending-dose, pharmacokinetic study. J Clin Pharmacol. Jan. 1997;37(1):25-30.

Foss et al., Subcutaneous methylnaltrexone reduces morphine-induced subjective effects in humans. Anesthesiology. 2001;95. Abstract A-817.

Foss et al., The efficacy of oral methylnaltrexone in decreasing the subjective effects of IV morphine. Anesth Analg. 1997;84. Abstract S484.

France et al., Morphine, saline and naltrexone discrimination in morphine-treated pigeons. J Pharm and Exper Ther. 1987;242: 195-202.

France et al., Comparison of naltrexone and quaternary naltrexone after systemic and intracerebroventricular administration in pigeons. Neuropharmacology. Jun. 1987;26(6):541-8.

France et al., Intracerebroventricular drug administration in pigeons. Pharmacol Biochem Behav. Nov. 1985;23(5):731-6.

Fraser et al., Methods for evaluating addiction liability. (A) "Attitude" of opiate addicts toward opiate-like drugs. (B) a short-term "direct" addiction test. J Pharmacol Exp Ther. Sep. 1961;133:371-87. Abstract Only.

Frässdorf et al., Morphine induces late cardioprotection in rat hearts in vivo: the involvement of opioid receptors and nuclear transcription factor kappaB. Anesth Analg. Oct. 2005; 101 (4):934-41.

Frederickson et al., Metkephamid, a Systemically Active Analog of Methionine Enkephalin with Potent Opioid ?—Receptor Activity. Science. 1991;211:603-05.

French et al., Purification and characterization of morphinone reductase from Pseudomonas putida M10. Biochem J. Jul. 1, 1994;301 (Pt 1):97-103.

Friedman et al., Opioid antagonists in the treatment of opioid-induced constipation and pruritus. Ann Pharmacother. Jan. 2001;35(1):85-91.

(56) References Cited

OTHER PUBLICATIONS

Funke et al., A proton and carbon-13 nuclear magnetic resonance study of three quaternary salts of naloxone and oxymorphone. J Chem Soc. 1986:735-8.

Galligan et al., Centrally mediated inhibition of small intestinal transit and motility by morphine in the rat. J Pharmacol Exp Ther. Aug. 1983;226(2):356-61. Abstract Only.

Gan et al., Consensus guidelines for managing postoperative nausea and vomiting. Anesth Analg. Jul. 2003;97(1):62-71. Review.

Gervitz, Targeted approach: methylnaltrexone blocks opioid-induced constipation and other peripheral side effects. Topics in Pain Management. 2005;21(1):6-8. Quiz on p. 11.

Giles et al., Quaternary opiate antagonists lower blood pressure and inhibit leucine-enkephalin responses. Eur J Pharmacol. Nov. 25, 1983;95(3-4):247-52.

Gmerek et al., Independent central and peripheral mediation of morphine-induced inhibition of gastrointestinal transit in rats. J Pharmacol Exp Ther. Jan. 1986;236(1):8-13.

Goumon et al., Ascaris suum, an intestinal parasite, produces morphine. J Immunol. Jul. 1, 2000; 165(1):339-43.

Green, Comparative effects of analgesics on pain threshold, respiratory frequency and gastrointestinal propulsion. Br J Pharmacol Chem other. Mar. 1959; 14(1):26-34.

Grigoriev et al., Clinical gastroenterology. Ministry of Health of the Russian Federation. Russian State Medical University. 2001;491-492. Russian.

Gupta et al., Angiogenesis: a curse or cure? Postgrad Med J. Apr. 2005;81(954):236-42.

Gupta et al., Morphine exaggerates retinopathy in transgenic sickle mice. Blood (ASH Annual Meeting Abstract) 106: Abstract 209.

Gupta et al., Morphine mimics VEGF in vascular endothelium by promoting pro-angiogenic and survival promoting signaling and angiogenesis. FASEB Journal. 2002; 16(4):A207. Abstract #182.12.

Gupta et al., Morphine stimulates angiogenesis by activating proangiogenic and survival-promoting signaling and promotes breast tumor growth. Cancer Res. Aug. 1, 2002;62(15):4491-8.

Gutstein et al., Role of inositol 1,4,5-trisphosphate receptors in regulating apoptotic signaling and heart failure. Heart Vessels. 1997;Suppl 12:53-7.

Guy et al., Chapter 1. Structural models of Na+, Ca2+, and K+ channels. In: Ion Channels and Genetic Diseases. Dawson et al., eds. 1995:1-28.

Hailes et al., Biological synthesis of the analgesic hydromorphone, an intermediate in the metabolism of morphine, by Pseudomonas putida M10. Appl Environ Microbiol. Jul. 1993;59(7):2166-70.

Hanif et al., Hypotensive effect of novel chimeric peptides of met-enkephalin and FMRFa. Regul Pept. Feb. 15, 2005;125(1-3):155-61.

He et al., Improvement of Bowel Dysfunction Caused by Opioid Analgesics: Research Advances on Methylnaltrexone. Chinese Journal of Clinical Rehabilitation. 2002;6(20):3104-05.

Hein et al., Pharmacological analysis of the discriminative stimulus characteristics of ethylketazocine in the rhesus monkey. J Pharmacol Exp Ther. Jul. 1981;218(1):7-15.

Hicks et al., Differential effects of the novel non-peptidic opioid 4-tyrosylamido-6-benzyl-1,2,3,4 tetrahydroquinoline (CGPM-9) on in vitro rat t lymphocyte and macrophage functions. Life Sci. May 4, 2001;68(24):2685-94.

Hirota et al., Loss of a gp 130 cardiac muscle cell survival pathway is a critical event in the onset of heart failure during biomechanical stress. Cell. Apr. 16, 1999;97(2): 189-98.

Ho et al., Beta-endorphin: peripheral opioid activity of homologues from six species. Int J Pept Protein Res. Apr. 1987;29(4):521-4.

Ho et al., Methylnaltrexone antagonizes opioid-mediated enhancement of HIV infection of human blood mononuclear phagocytes. J Pharmacol Exp Ther. Dec. 2003;307(3): 1158-62. Epub Oct. 14, 2003.

Ho et al., Suppression of immunological functions in morphine addicted mice. NIDA Res Monogr. 1986;75:599-602.

Hoffmann et al., [Calcium in the prevention of stress ulcer in the rat] Langenbecks Arch Chir. 1976;Suppl:228-32. German.

Simonin et al., kappa-Opioid receptor in humans: cDNA and genomic cloning, chromosomal assignment, functional expression, pharmacology, and expression pattern in the central nervous system. Proc Natl Acad Sci USA. Jul. 18, 1995;92(15):7006-10.

Simonin et al., The human delta-opioid receptor: genomic organization, cDNA cloning, functional expression, and distribution in human brain. Mol Pharmacol. Dec. 1994;46(6):1015-21. Abstract Only.

Soldani et al., Central and peripheral involvement of mu receptors in gastric secretory effects of opioids in the dog. Eur J Pharmacol. Nov. 19, 1985;117(3):295-301.

Solvason et al., Naltrexone blocks the expression of the conditioned elevation of natural killer cell activity in BALB/c mice. Brain Behav Immun. Sep. 1989;3(3):247-62.

Stanski et al., Kinetics of intravenous and intramuscular morphine. Clin Pharmacol Ther. Jul. 1978;24(1):52-9.

Steele et al., HIV-1 Infection and Opioid Administration Modulate the Expression of Chemokine Receptors. Drug and Alcohol Dependence. 2000:60(Supp 1 ):S212. Abstract 599.

Stefano et al., Delta2 opioid receptor subtype on human vascular endothelium uncouples morphine stimulated nitric oxide release. Int J Cardiol. Apr. 30, 1998;64 Suppl 1:S43-51.

Stefano et al., Long-term exposure of human blood vessels to HIV gp120, morphine, and anandamide increases endothelial adhesion of monocytes: uncoupling of nitric oxide release. J Cardiovasc Pharmacol. Jun. 1998;31(6):862-8.

Stefano et al., Morphine enhances nitric oxide release in the mammalian gastrointestinal tract via the micro(3) opiate receptor subtype: a hormonal role for endogenous morphine. J Physiol Pharmacol. Mar. 2004;55(1 Pt 2):279-88.

Stefano et al., Presence of the mu3 opiate receptor in endothelial cells. Coupling to nitric oxide production and vasodilation. J Biol Chem. Dec. 22, 1995;270(51):30290-3.

Steinbrook et al., An opioid antagonist for postoperative ileus. N Engl J Med. Sep. 27, 2001;345(13):988-9.

Stephenson et al., Methylnaltrexone reverses opioid-induced constipation. Lancet Oncol. Apr. 2002;3(4):202.

Sternini et al., The opioid system in the gastrointestinal tract. Neurogastroenterol Motil. Oct. 2004;16 Suppl 2:3-16.

Stewart et al., Central and peripheral actions of morphine on intestinal transit. J Pharmacol Exp Ther. Jun. 1978;205(3):547-55.

Stiene-Martin et al., Regional, developmental, and cell cycle-dependent differences in mu, delta, and kappa-opioid receptor expression among cultured mouse astrocytes. Glia. Mar. 1998;22(3):249-59.

Suzuki et al., Morphine suppresses lymphocyte apoptosis by blocking p53-mediated death signaling. Biochem Biophys Res Commun. Sep. 5, 2003;308(4):802-8.

Swan, et al., NIDA plays key role in studying links between AIDS and drug abuse. AIDS Research, NIDA Notes. 1995; 10(3):1-4.

Sykes, Oral naloxone in opioid-associated constipation. Lancet. Jun. 15, 1991;337(8755):1475.

Sykes, Chapter 9. Using oral naloxone in management of opioid bowel dysfunction. Handbook of Opioid Bowel Syndrome, New York, Haworth Medical Press, Yuan, C-S, editor. 2005:175-95.

Szabo et al., Interactions of opioid receptors, chemokines, and chemokine receptors. Adv Exp Med Biol. 2001;493:69-74.

Taguchi et al., Selective postoperative inhibition of gastrointestinal opioid receptors. N Engl J Med. Sep. 27, 2001;345(13):935-40.

Talley et al., Pharmacologic therapy for the irritable bowel syndrome. Am J Gastroenterol. Apr. 2003;98(4):750-8.

Tavani et al., Morphine is most effective on gastrointestinal propulsion in rats by intraperitoneal route: evidence for local action. Life Sci. Dec. 8, 1980;27(23):2211-7.

Tegeder et al., Opioids as modulators of cell death and survival—unraveling mechanisms and revealing new indications. Pharmacol Rev. Sep. 2004;56(3):351-69.

Thomas et al., A phase III double-blind placebo-controlled trial of methylnaltrexone (MNTX) for opioid-induced constipation (OIC) in advanced medical illness (AMI). Abstract No. LBA8003 from the 2005 ASCO Annual Meeting. 3 pages.

(56) References Cited

OTHER PUBLICATIONS

Thomas et al., Amelioration of peripheral side effects of opioids: clinical experience with methylnaltrexone (MNTX). Proc World Congr Anesth. 2004:107. Abstract Only.
Thompson et al., Laxatives: clinical pharmacology and rational use. Drugs. Jan. 1980; 19(1):49-58.
Thompson et al., Opioid stimulation in the ventral tegmental area facilitates the onset of maternal behavior in rats. Brain Res. Dec. 16, 1996;743(1-2):184-201.
Tomiyasu et al., Analysis of intercostal nerve damage associated with chronic post-thoracotomy pain. Anesthesiology. 2001;95. Abstract A-964.
Tryoen-Toth et al., Regulation of kappa-opioid receptor mRNA level by cyclic AMP and growth factors in cultured rat glial cells. Brain Res Mol Brain Res. Mar. 30, 1998;55(1): 141-50.
Ukai et al., Suppression of deprivation-induced water intake in the rat by opioid antagonists: central sites of action. Psychopharmacology (Berl). 1987;91(3):279-84.
Uwai et al., Syntheses and receptor-binding studies of derivatives of the opioid antagonist naltrexone. Bioorg Med Chem. Jan. 15, 2004;12(2):417-21.
Valentino et al., Quaternary naltrexone: evidence for the central mediation of discriminative stimulus effects of narcotic agonists and antagonists. J Pharmacol Exp Ther. Jun. 1981;217(3):652-9.
Valentino et al., Receptor binding, antagonist, and withdrawal precipitating properties of opiate antagonists. Life Sci. Jun. 20, 1983;32(25):2887-96.
Vallejo et al., Opioid therapy and immunosuppression: a review. Am J Ther. Sep.-Oct. 2004; 11(5):354-65.
Vaughan et al., Human antibodies by design. Nat Biotechnol. Jun. 1998;16(6):535-9.
Vermiere et al., Stability and compatibility of morphine. International Journal of Pharmaceutics. 1999;187:17-51.
Waldhoer et al., Opioid receptors. Annu Rev Biochem. 2004;73:953-90.
Walker, et al., Role of central versus peripheral opioid receptors in analgesia induced by repeated administration of opioid antagonists. Psychopharmacology. 1991; 104(2): 164-6.
Walsh et al., The symptoms of advanced cancer: relationship to age, gender, and performance status in 1,000 patients. Support Care Cancer. May 2000;8(3): 175-9. Abstract Only.
Wang et al., A non-peptide substance P antagonist (CP-96,345) inhibits morphine-induced NF-kappa B promoter activation in human NT2-N neurons. J Neurosci Res. Feb. 15, 2004;75(4):544-53.
Wang et al., Determination of tungsten in bulk drug substance and intermediates by ICP-AES and ICP-MS. J Pharm Biomed Anal. May 1999; 19(6):937-43. Abstract Only.
Wang et al., Human mu opiate receptor. cDNA and genomic clones, pharmacologic characterization and chromosomal assignment. FEBS Lett. Jan. 31, 1994 ;338(2):217-22. Abstract Only.
Wang et al., Mobilization of calcium from intracellular stores as one of the mechanisms underlying the antiopioid effect of cholecystokinin octapeptide. Peptides. Sep.-Oct. 1992;13(5):947-51.
Wang et al., Morphine negatively regulates interferon-gamma promoter activity in activated murine T cells through two distinct cyclic AMP-dependent pathways. J Biol Chem. Sep. 26, 2003;278(39):37622-31. Epub Jul. 3, 2003.
Wang et al., The immunosuppressive effects of chronic morphine treatment are partially dependent on corticosterone and mediated by the mu-opioid receptor. J Leukoc Biol. May 2002;71(5):782-90.
Warren et al., Effects of quaternary naltrexone and chlordiazepoxide in squirrel monkeys with enhanced sensitivity to the behavioral effects of naltrexone. J Pharmacol Exp Ther. Nov. 1985;235(2):412-7.
Wei et al., Effects of Subcutaneous Methylnaltrexone on Morphine-Induced Gut Motility Changes: A Clinical Trial. Abstracts of the 2002 Annual Meeting of the American Society for Clinical Pharmacology and Therapeutics. Atlanta, Georgia, USA. Mar. 24-27, 2002. Clin Pharmacol Ther. Feb. 2002;71(2):P11. Abstract MPI-26.
Wei et al., Opioid-induced immunosuppression: is it centrally mediated or peripherally mediated? Biochem Pharmacol. Jun. 1, 2003 ;65(11): 1761-6.
Wei et al., Pharmacokinetics of subcutaneous methylnaltrexone: different route administration comparison. 2001. ASA Annual Meeting Abstracts. Oct. 14-18, 2001. Chicago, IL. Abstract A-962.
[No Author Listed] European Medicines Agency, Impurities in New Drug Substances, Oct. 2006; 15 pages.
[No Author Listed] Mallinckrodt Pharmaceuticals, Methylnaltrexone Bromide, Product Specifications Effective Mar. 2014; 1 page.
[No Author Listed] Mallinckrodt Pharmaceuticals, Methylnaltrexone Bromide, Technical Package 2014; 3 pages.
[No Author Listed] Monograph for Naltrexone, U.S. Pharmacopeia USP 29, NF 24, 2006; pp. 1476-1478, 2556-2557.
[No Author Listed] Prefilled Syringes: The Tread for Growth Strengthens. ONdrugDelivery Ltd. (G. Furness, publisher), 2006; 32 pages.
Balls, Concerning Pseudomorphine. J Biol Chem. 1927; 71:537-542.
Bauer, Lehrbuch der Pharmazeutischen Technologie, 7th Edition. Wissenschaftliche Verlagsgesellschaft mbH, 2002; Chapter 9: p. 240. German.
Bhatt et al., Cleavage of Ethers. Synthesis, 1983; 4:249-282.
Broadhead, Parenteral Dosage Form. Pharmaceutical Preformulation and Formulation (M. Gibson, ed.), 2001; pp. 331-354.
U.S. Appl. No. 60/461,611, filed Apr. 8, 2003.
Feltkamp et al., Pharmazeutische Qualit?tskontrolle. Georg Thieme Verlag, 1983; pp. 502-504. German.
International Preliminary Report on Patentability for PCT/US2007/017430 mailed Feb. 19, 2009.
International Preliminary Report on Patentability for PCT/US2007/019556 mailed Mar. 19, 2009.
International Search Report and Written Opinion for PCT/US2007/017430 mailed May 7, 2008.
International Search Report and Written Opinion for PCT/US2007/019556 mailed Mar. 12, 2008.
Jenke, Suitability-for-Use Considerations for Prefilled Syringes. Downloaded from http://www.pharmtech.com/suitability-use-considerations-prefilled-syringes, Apr. 1, 2008.
Jiang et al., 2009. Tungsten-Induced Protein Aggregation: Solution Behavior. J of Pharma Sci, 2009; 98(12):4695-4710.
Kim (The Physical State of Mannitol after Freeze-Drying: Effects of Mannitol Concentration, Freezing Rate, and a Noncrystallizing Cosulute, Journal of Pharmaceutical Sciences 1998, vol. 87, No. 8 pp. 931-935).
Lachman et al., The Theory and Practice of Industrial Pharmacy, Third Indian Edition. Varghese Publishing House, 1987; pp. 190-193 and 764.
Lindholm, Test Report: Methylnaltrexone Bromide pH Testing. Fresnius Kabi, Sep. 21, 2015.
Mutschler et al. Arzneimittelwirkungen: Lehrbuch der Pharmakologie und Toxikologie, 8th Edition. Wissenschaftliche Verlagsgesellschaft mbH, 2001; pp. 214-219. German.
Novak et al., Tungsten (V) Complexes of Ethylenediaminetetraacetic Acid. J Inorg Nucl Chem, 1973; 36:1061-1065.
Opposition filed on Mar. 6, 2009 in Ecuadoran Patent Application No. SP-8-8752.
Positive Results from Phase 3 Clinical Study of Methylnaltrexone Treatment for Opioid-Induced Constipation Presented at Digestive Disease Week Conference, May 23, 2006 (http://files.shareholder.com/downloads/PGNX/0x0x40529/bfba0030-5977-4a52-b228-91ae6b7daf8b/198253.pdf).
Quarry et al., Investigation of 4,5-epoxymorphinian degradation during analysis by HPLC. J Pharma Biomed Anal. 2002; 30: 99-104.
Remington, The Science and Practice of Pharmacy, 19th Edition. Mack Publishing Company, 1995; vol. II: p. 1486.

(56) References Cited

OTHER PUBLICATIONS

Rios et al., 2007. Big Shot: Developments in Prefilled Syringes. Downloaded from http://www.pharmtech.com/big-shot-developments-prefilled-syringes, Mar. 2, 2007.
Rowe et al., Handbook of Pharmaceutical Excipients, 4th Edition. Pharmaceutical Press, 2003; pp. 225-228.
Steele, Preformulation as an aid to product design in early drug development. Pharmaceutical Preformulation and Formulation (M. Gibson, ed.), 2001, pp. 175-237.
Voet et al., Biochemistry, German Edition. VCH Verlagsgesellschaft mbH, reprinted 1994; pp. 36-39.
Voight, Lehrbuch der pharmazeutischen Technologie, 6th Edition. VEB Verlag Volk und Gesundheit, 1987; pp. 395 and 503. German.
Written Opinion of PCT/US2004/010998 mailed Sep. 1, 2004.
Written Opinion of PCTUS2004/010996 mailed Aug. 16, 2004.
Yeh et al., Stability of morphine in aqueous solution III. J Pharma Sci 1961; 50:35-42.
Swift et al., "BIOT 15—Tungsten, prefilled syringes and protein aggregation," Biophysical and Biomolecular Symposium: Protein Stability. The 234th ACS National Meeting, Boston, MA, Aug. 19-23, 2007. Abstract. Retrieved on May 25, 2016 at<oasys2.confex.com/acs/234nm/techprogram/P1096944.HTM>, 1 Page.
Kotz et al., "Acids and Bases," Chemistry & chemical reactivity. Saunders College Publishing, pp. 551-600 (1987).
[No Author Listed] Remington, The Science and Practice of Pharmacy, 19th Edition. Mack Publishing Company, 1995; pp. 639-647 and 1447-1462.
Fawcett et al. "Formulation and stability of naltrexone oral liquid for rapid withdrawal from methadone," Ann Pharmacother. 31(11):1291-5 (1997).
Rosow, "Methylnaltrexone: reversing the gastrointestinal effects of opioids," Anesthesiology. 87(4):736-7 (1997).
Vaczek, "Promoting dosing accuracy with prefilled syringes," Syringes. <packagingdigest.com/syringes/pmp-promoting-dosing-accuracy-with-prefilled-syringes-2007-04-29> (2007), 7 pages.
Guo et al. "Group 5 and group 6 metal halides as very efficient catalysts for acylative cleavage of ethers," Tetrahedron. 58: 7327-34 (2002).

* cited by examiner

Initial Chromatogram

STABLE PHARMACEUTICAL FORMULATIONS OF METHYLNALTREXONE

RELATED APPLICATIONS

The present application is a continuation of U.S. patent application Ser. No. 12/639,892, filed on Dec. 16, 2009, which is a continuation of U.S. patent application Ser. No. 10/821,811, filed on Apr. 8, 2004, which claims priority to U.S. Provisional Application No. 60/461,611, filed Apr. 8, 2003, the entire contents of each of which are hereby incorporated by reference herein.

FIELD OF THE INVENTION

This invention relates to methylnaltrexone pharmaceutical preparations, methylnaltrexone formulations, methylnaltrexone kits, and methods of making the same.

BACKGROUND OF THE INVENTION

Quaternary amine opioid antagonist derivatives have been shown to have utility in a number of contexts. They are considered peripherally acting only, and, therefore, find particular utility in reducing the side-effects of opioids without reducing the analgesic effect of opioids. Such side effects include nausea, emesis, dysphoria, pruritis, urinary retention, bowel hypomotility, constipation, gastric hypomotility, delayed gastric emptying and immune suppression. The utility of these peripherally acting opioid antagonists is not limited to reducing side-effects stemming from opioid analgesic treatment. Instead, these derivatives also have utility in circumstances where endogenous opioids alone (or in conjunction with exogenous opioid treatment) cause undesirable conditions such as ileus and other such conditions including, but not limited to, those mentioned above.

Methylnaltrexone is a quaternary amine opioid antagonist derivative, discovered in the mid-70s. Methylnaltrexone and some of its uses are described in U.S. Pat. Nos. 4,176,186, 4,719,215, 4,861,781, 5,102,887, 5,972,954, and 6,274,591. Stable formulations of methylnaltrexone, however, have heretofore not existed. Methylnaltrexone apparently was assumed to have a structure that was inherently stable. The stability of a pharmaceutical composition in solution, however, is not necessarily predictable either over time when stored at room temperature or when autoclaved.

Naloxone is an opioid antagonist that acts both centrally and peripherally. It differs structurally from methylnaltrexone and would be expected to have a different stability in solution. An allegedly stable formulation of naloxone is described in U.S. Pat. No. 5,866,154.

Surprisingly, it has been discovered that methylnaltrexone is unusually unstable. It further has been discovered that methylnaltrexone has certain degradation products different from those of naloxone. It also has been discovered that critical parameters and conditions are required for stable formulations of methylnaltrexone.

SUMMARY OF THE INVENTION

In one aspect, the invention provides a composition or preparation that is a solution of methylnaltrexone or a salt thereof, wherein the preparation after autoclaving has a concentration of methylnaltrexone degradation products that does not exceed 2% of the methylnaltrexone or salt thereof in the preparation. Preferably, the concentration of such degradation products does not exceed 1.5%, 1%, 0.5%, 0.25%, or even 0.125% of the methylnaltrexone or salt thereof in the preparation. The composition or preparation can contain one of, any combination of, or all of a chelating agent, a buffering agent, an anti-oxidant, a cryoprotecting agent, an isotonicity agent and an opioid. The preferred chelating agent is disodium edetate or a derivative thereof. The disodium edetate preferably is at a concentration ranging from between 0.001 and 100 mg/nal, more preferably 0.05 to 25.0 mg/ml, and even more preferably, 0.1 to 2.5 mg/ml. A preferred buffering agent is citrate buffer. The citrate buffer typically is in a concentration ranging from 0.001 to 100.0 mM, preferably from 0.1 to 10 mM, and more preferably, 0.1 to 5.0 mM. A preferred cryoprotecting agent is mannitol.

The composition or preparation preferably has a pH that does not exceed 4.25. More preferably, the pH ranges from 2.0 to 4.0, 3.0 to 4.0, and most preferably, from 3.0 to 3.5.

According to another aspect of the invention, a composition or preparation is provided, which includes a solution of methylnaltrexone or a salt thereof, wherein the preparation after storage at about room temperature for six months has a concentration of methylnaltrexone degradation products that does not exceed 2% of the methylnaltrexone in the preparation. The concentration of the methylnaltrexone degradation products preferably does not exceed 1.5%, 1.0%, 0.5%, 0.25%, and even 0.125% of the methylnaltrexone in the preparation. The composition or preparation can contain one of, any combination of, or all of a chelating agent, a buffering agent, an anti-oxidant, a cryoprotecting agent, an isotonicity agent and an opioid. The preferred chelating agent and concentrations are as described above. The preferred buffering agent and concentrations are as described above. Preferably, the composition or preparation has a pH that does not exceed 4.25. The preferred pHs and ranges are as described above.

According to another aspect of the invention, a stable composition or preparation is provided. The composition or preparation is a solution of methylnaltrexone or a salt thereof wherein the pH is below 4.25. Preferably, the pH is between 2.75 and 4.25, more preferably, between 3.0 and 4.0, and most preferably, between 3.0 and 3.5. According to conventional procedures, pH can be adjusted with an acid. Examples of acids useful for this purpose include hydrochloric acid, citric acid, sulfuric acid, acetic acid, and phosphoric acid. The stable composition or preparation can also include any one of, any combination of, or all of a chelating agent, a buffering agent, an isotonicity agent, an antioxidant, a cryogenic agent, and an opioid.

According to another aspect of the invention, a stable composition or preparation is provided. The composition or preparation is a solution of methylnaltrexone or salt thereof, wherein the solution further comprises a chelating agent in an amount sufficient to inhibit degradation of the methylnaltrexone or salt thereof, whereby the amount is such that the composition or preparation after autoclaving has a concentration of methylnaltrexone degradation products that does not exceed 0.5%, 0.25% or even 0.125% of the methylnaltrexone or salt thereof in the composition or preparation. The composition or preparation can further include any one of, any combination of, or all of a buffering agent, an isotonicity agent, an antioxidant and an opioid. Preferred chelating agents, buffering agents and pHs are as described above.

According to another aspect of the invention, a composition or preparation is provided. The composition or preparation is a solution of methylnaltrexone or salt thereof in at least one methylnaltrexone degradation inhibiting agent.

The agent can be any one of, any combination of, or all of a chelating agent, a buffering agent, and an antioxidant, provided that the solution has a pH ranging from 2.0 to 6.0. The degradation inhibiting agent is present in an amount sufficient to render the composition or preparation stable, wherein the composition or preparation is processed under at least one sterilization technique, and wherein the composition or preparation is substantially free of methylnaltrexone degradation products. The composition or preparation can be stable to storage for at least six months, at least twelve months, or at least twenty-four months, at about room temperature. Preferably, the composition or preparation is stable after autoclaving. The composition or preparation further may include either or both of an isotonicity agent and an opioid. Preferably, the pH of the solution is between 2.75 and 4.25, more preferably, between 3.0 and 4.0, and most preferably, between 3.0 and 3.5.

In any one of the foregoing aspects of the invention, the composition or preparation can be a pharmaceutical composition.

In any one of the foregoing aspects of the invention, the methylnaltrexone can be present in a therapeutically effective amount. In some embodiments, the concentration of methylnaltrexone ranges from 0.01 to 100 mg/ml. In other embodiments, the methylnaltrexone concentration ranges between 0.1 and 100.0 mg/ml. In other embodiments, the methylnaltrexone ranges between 1.0 and 50.0 mg/ml.

In any one of the foregoing embodiments, the methylnaltrexone can be present in an amount sufficient to treat nausea, emesis, dysphoria, pruritus, urinary retention, ileus, post-operative ileus, post-partum ileus, paralytic ileus, bowel hypomotility, constipation, gastric hypomotility, delayed gastric emptying, decreased biliary secretion, decreased pancreatic secretion, biliary spasm, increased sphincter tone, cutaneous flushing, impaction, sweating, inhibition of gastrointestinal motility, inhibition of gastric emptying, gastrointestinal dysfunction, incomplete evacuation, bloating, abdominal distention, increased gastroesophageal reflux, hypotension, bradycardia, irritable bowel syndrome, or immunosuppression.

In any of the foregoing embodiments, the methylnaltrexone can be present in an amount sufficient to accelerate discharge from hospital post-surgery (including abdominal surgeries such as rectal resection, colectomy, stomach, esophageal, duodenal, appendectomy, hysterectomy, or non-abdominal surgeries such as orthopedic, trauma injuries, thoracic or transplantation), for example, by accelerating bowel sounds after surgery, or speeding the time to first food intake or first bowel movement. In other important embodiments, the amount is sufficient to induce taxation. This has particular application where the subject is a chronic opioid user.

In any one of the foregoing embodiments, the solution of methylnaltrexone or salt thereof may be contained in a sealed container such as a bottle, an infusion bag, a syringe, a vial, a vial with a septum, an ampoule, an ampoule with a septum, or a syringe. The container may include indicia indicating that the solution has been autoclaved or otherwise subjected to a sterilization technique.

According to another aspect of the invention, any of the foregoing embodiments is lyophilized, preferably in the presence of a cryoprotecting agent. The invention therefore provides a lyophilized preparation of methylnaltrexone. Preferably, the lyophilized preparation is a stable preparation, containing less than 1%, less than 0.5%, less than 0.25% and even less than 0.125% methylnaltrexone degradation product. The preparation can contain a cryoprotecting agent, which preferably is neutral or acidic in water.

According to another aspect of the invention, a product is provided. The product is a stable lyophilized formulation of methylnaltrexone, wherein the formulation upon reconstitution and water at a concentration of 20 mg/ml has a pH of between 2 and 6. In some embodiments, the formulation upon reconstitution has a pH of about 2, about 3, about 4, about 5, or about 6. The formulation can include a cryoprotecting agent present in amounts sufficient to render the formulation stable. The cryoprotecting agent in important embodiments are polymerized carbohydrates. A preferred cryoprotecting agent is mannitol. Any one of the foregoing solutions described above can be lyophilized. It therefore is an aspect of the invention that such materials include one or any combination of a buffering agent, a chelating agent, an antioxidant, and an isotonicity agent. Preferred materials are as described above.

According to still another aspect of the invention, a product is provided that includes methylnaltrexone and the degradation inhibiting agent selected from the group consisting of a chelating agent, a buffering agent, an antioxidant, and combinations thereof, wherein the degradation inhibiting agent is present in an amount sufficient to render stable the solution of the product containing a concentration of 20 mg/ml methylnaltrexone in water. Preferably, the product when in solution at a concentration of 20 mg/ml methylnaltrexone yields a pH of between 2 and 6.

According to another aspect of the invention, a pharmaceutical preparation is provided. The pharmaceutical preparation contains methylnaltrexone, sodium chloride, citric acid, trisodium citrate, and disodium edetate. In one important embodiment, the methyl naltrexone is present between 20 and 40 mg/ml, the sodium chloride is present between 2 and 6 mg/ml, the citric acid is present between 0.05 and 0.1 mg/ml, the trisodium citrate is present between 0.025 and 0.075 mg/ml, and the disodium edetate is present between 0.5 and 1.0 mg/ml.

The buffering agent may be any pharmaceutically acceptable buffering agent. Common buffering agents include citric acid, sodium citrate, sodium acetate, acetic acid, sodium phosphate and phosphoric acid, sodium ascorbate, tartaric acid, maleic acid, glycine, sodium lactate, lactic acid, ascorbic acid, imidazole, sodium bicarbonate and carbonic acid, sodium succinate and succinic acid, histidine, and sodium benzoate and benzoic acid. The preferred buffering agent is a citrate buffering agent.

The chelating agent may be any pharmaceutically acceptable chelating agent. Common chelating agents include ethylenediaminetetraacetic acid (EDTA) and derivatives thereof, citric acid and derivatives thereof, niacinamide and derivatives thereof, and sodium desoxycholate and derivatives thereof. The preferred chelating agent is disodium edetate.

The antioxidant may be any pharmaceutically acceptable antioxidant. Common antioxidants include those selected from the group consisting of an ascorbic acid derivative, butylated hydroxy anisole, butylated hydroxy toluene, alkyl gallate, sodium meta-bisulfite, sodium bisulfite, sodium dithionite, sodium thioglycollic acid, sodium formaldehyde sulfoxylate, tocopherol and derivatives thereof, monothioglycerol, and sodium sulfite. The preferred antioxidant is monothioglycerol.

The cryoprotecting agent may be any pharmaceutically acceptable cryoprotecting agent. Common cryoprotecting agents include histidine, polyethylene glycol, polyvinyl pyrrolidine, lactose, sucrose, and mannitol. Improtant cryoprotecting agents are polyols. The preferred cryoprotecting agent of the invention is mannitol.

The opioid can be any pharmaceutically acceptable opioid. Common opioids are those selected from the group consisting of alfentanil, anileridine, asimadoline, bremazocine, burprenorphine, butorphanol, codeine, dezocine, diacetylmorphine (heroin), dihydrocodeine, diphenoxylate, fedotozine, fentanyl, funaltrexamine, hydrocodone, hydromorphone, levallorphan, levomethadyl acetate, levorphanol, loperamide, meperidine (pethidine), methadone, morphine, morphine-6-glucoronide, nalbuphine, nalorphine, opium, oxycodone, oxymorphone, pentazocine, propiram, propoxyphene, remifentanyl, sufentanil, tilidine, trimebutine, and tramadol.

The isotonicity agent can be any pharmaceutically acceptable isotonicity agent. Common isotonicity agents include those selected from the group consisting of sodium chloride, mannitol, lactose, dextrose, glycerol, and sorbitol. The preferred isotonicity agent is mannitol.

The pharmaceutical preparation may optionally comprise a preservative. Common preservatives include those selected from the group consisting of chlorobutanol, parabens, thimerosol, benzyl alcohol, and phenol.

According to another aspect of the invention, a method is provided for preparing an autoclaved preparation of a solution of methylnaltrexone or salts thereof, whereby the autoclaved preparation has a concentration of methylnaltrexone degradation products that does not exceed 2% of the methylnaltrexone or salt thereof in the preparation. The method involves providing a solution, having a pH of 4.25 or less, of methylnaltrexone or a salt thereof, and being substantially free of methylnaltrexone degradation products, and autoclaving the solution. The solution can contain, optionally, any one of, any combination of, or all of a chelating agent, an isotonicity agent, a buffering agent, an antioxidant, a cryoprotecting agent, and an opioid. Preferably, the pH of the solution ranges from 2.0 to 4.0. More preferably, from 3.0 to 4.0, and most preferably from 3.0 to 3.5. Preferred chelating agents, isotonicity agents, buffering agents, antioxidants, cryoprotecting agents, and opioids are as described above. Preferred concentrations of methylnaltrexone, likewise, are as described above.

According to another aspect of the invention, a method is provided for preparing an autoclaved preparation. The preparation has a concentration of methylnaltrexone degradation products that does not exceed 2% of the methylnaltrexone or salt thereof in the preparation. The method involves providing a solution containing methylnaltrexone or salt thereof and a chelating agent, the solution being substantially free of methylnaltrexone degradation products, and then autoclaving the solution. The chelating agent is present in an amount sufficient to protect the preparation against substantial unwanted degradation of methylnaltrexone or its salt, and maintain the solution to be substantially free of methylnaltrexone degradation products. Preferred chelating agents and concentrations thereof are as described above. The preparation may include, optionally, any one of, any combination of, or all of a buffering agent, an isotonicity agent, an antioxidant, a cryoprotecting agent, and an opioid. Preferred buffering agents, isotonicity agents, antioxidants and opioids, as well as concentrations, are as described above. Preferred pHs of the solution likewise are as described above. Preferably, the degradation products after autoclaving do not exceed 1.5%, 1%, 0.5%, 0.25% or even 0.125%.

According to another aspect of the invention, a method is provided for inhibiting the formation of methylnaltrexone degradation products in a preparation that is a solution of methylnaltrexone or salts thereof. The method involves preparing an aqueous solution containing at least one methylnaltrexone degradation inhibiting agent selected from the group consisting of a chelating agent, a buffering agent, an antioxidant, a cryoprotecting agent, and combinations thereof. A powdered source of methylnaltrexone or salt thereof is dissolved into the solution to form the preparation. The preparation has or is adjusted without addition of a pH-adjusting base to have a pH of between 2 and 6. More preferably, the pharmaceutical preparation is adjusted to have a pH ranging from 3 to 5, more preferably, 3 to 4, and most preferably, 3.0 to 3.5. An isotonicity agent may be added to the solution. Likewise, an opioid may be added to the solution.

In any one of the foregoing aspects of the invention, the preparation can be a pharmaceutical preparation.

According to another aspect of the invention, a method is provided for preparing a stable pharmaceutical preparation that is an aqueous solution of methylnaltrexone or salts thereof to inhibit formation of methylnaltrexone degradation products. A solution is provided containing methylnaltrexone or salts thereof and at least one methylnaltrexone degradation inhibiting agent. The solution is processed under at least one sterilization technique prior to and/or after terminal filling the solution in a sealable container to form the stable pharmaceutical preparation, wherein the method is carried out without the addition of pH-adjusting base to the solution. The methylnaltrexone degradation inhibiting agent can be selected from the group consisting of a chelating agent, a buffering agent, an antioxidant, and combinations thereof. An isotonicity agent can be added. A cryoprotecting agent can also be added. Likewise, an opioid can be added. Preferred chelating agents, buffering agents, antioxidants, isotonicity agents, cryoprotecting agents, and opioids are as described above. Preferred concentrations are as described above. The solution may be processed to adjust the pH. This is preferably done using an acid. Most preferably, the solution is adjusted to a range between a pH of 2 and 6, more preferably, between 3 and 5, 3 and 4, and most preferably between 3.0 and 3.5. The material can be contained in a sealed container. The container can be purged with nitrogen and/or sparged to eliminate oxygen.

In some embodiments of the invention, parenteral formulations are provided. In one embodiment, the formulation made by dissolving methylnaltrexone diluted in water, to which mannitol is added. The solution is then filter sterilized followed by lyophilization. Therefore, the product may be provided in lyophilized form, and in combination with certain cryoprotectants such as mannitol or lactose. Optionally, a reconstituting diluent is provided, such as a physiological saline diluent.

According to another aspect of the invention, a kit is provided. The kit is a package containing a sealed container comprising any one of the preparations described above, together with instructions for use. The kit can also include a diluent container containing a pharmaceutically acceptable diluent. The kit can further comprise instructions for mixing the preparation and the diluent. The diluent can be any pharmaceutically acceptable diluent. Well known diluents include 5% dextrose solution and physiological saline solution. The container can be an infusion bag, a sealed bottle, a vial, a vial with a septum, an ampoule, an ampoule with a septum, an infusion bag or a syringe. The kit further can contain an opioid container containing an opioid. The containers can optionally include indicia indicating that the containers have been autoclaved or otherwise subjected to sterilization techniques. The kit can include instructions for administering the various solutions contained in the containers to subjects.

The invention also involves methods of treatment. According to another aspect of the invention, a method is provided for treating a subject in need of such treatment with an effective amount of methylnaltrexone or a salt thereof. The method involves administering to the subject an effective amount of methylnaltrexone or salt thereof in any one of the pharmaceutical preparations described above, detailed herein, and/or set forth in the claims. In one aspect, the method is a method for inhibiting a peripheral opioid receptor in a human subject. In another aspect, the method is for reducing a side-effect of opioid treatment. In another aspect, the method is for treating any one of a condition selected from the group consisting of nausea, emesis, dysphoria, pruritus, urinary retention, ileus, post-operative ileus, post-partumileus, parallytic ileus, bowel hypomotility, constipation, gastric hypomotility, delayed gastric emptying, decreased biliary secretion, decreased pancreatic secretion, biliary spasm, increased sphincter tone, cutaneous flushing, impaction, sweating, inhibition of gastrointestinal motility, inhibition of gastric emptying, gastrointestinal dysfunction, incomplete evacuation, bloating, abdominal distension, increased gastroesophageal reflux, hypotension, bradycardia, irritable bowel syndrome, or immunosuppression.

In any of the foregoing embodiments, the methylnaltrexone can be present in an amount sufficient to accelerate discharge from hospital post-surgery, accelerate bowel sounds after surgery, or induce laxation.

The subject can be any subject in need of such treatment. Important subjects include those receiving opioids including opioids for pain, cancer or surgical patients, or immunosuppressed or immunocompromised patients (including HIV infected patients), patients with advanced medical illness, terminally ill patients, patients with neuropathies, patients with rheumatoid arthritis, patients with osteoarthritis, patients with chronic pack pain, patients with spinal cord injury, patients with chronic abdominal pain, patients with chronic pancreatic pain, patients with pelvic/perineal pain, patients with fibromyalgia, patients with chronic fatigue syndrome, patients with migraine or tension headaches, patients on hemodialysis, and patients with sickle cell anemia.

In the foregoing description, applicants have described the invention in connection with methylnaltrexone or salts thereof. Such salts include, but are not limited to, bromide salts, chloride salts, iodide salts, carbonate salts, and sulfate salts. It should be understood, however, that methylnaltrexone is a member of a class of compounds known as quaternary derivatives of noroxymorphone, as disclosed in U.S. Pat. No. 4,176,186, the entire disclosure of which is incorporated herein by reference. It is believed that the invention extends to any such quaternary derivative of noroxymorphone, and the invention is intended to embrace pharmaceutical preparations, methods and kits containing such derivatives. Another aspect of the invention then embraces the foregoing summary but read in each aspect as if any such derivative is substituted wherever "methylnaltrexone" appears. Likewise, the invention also embraces each and every claim read as if the term "quaternary derivative of noroxymorphone" were substituted whenever "methylnaltrexone" appears.

DETAILED DESCRIPTION OF THE INVENTION

Figure 1:
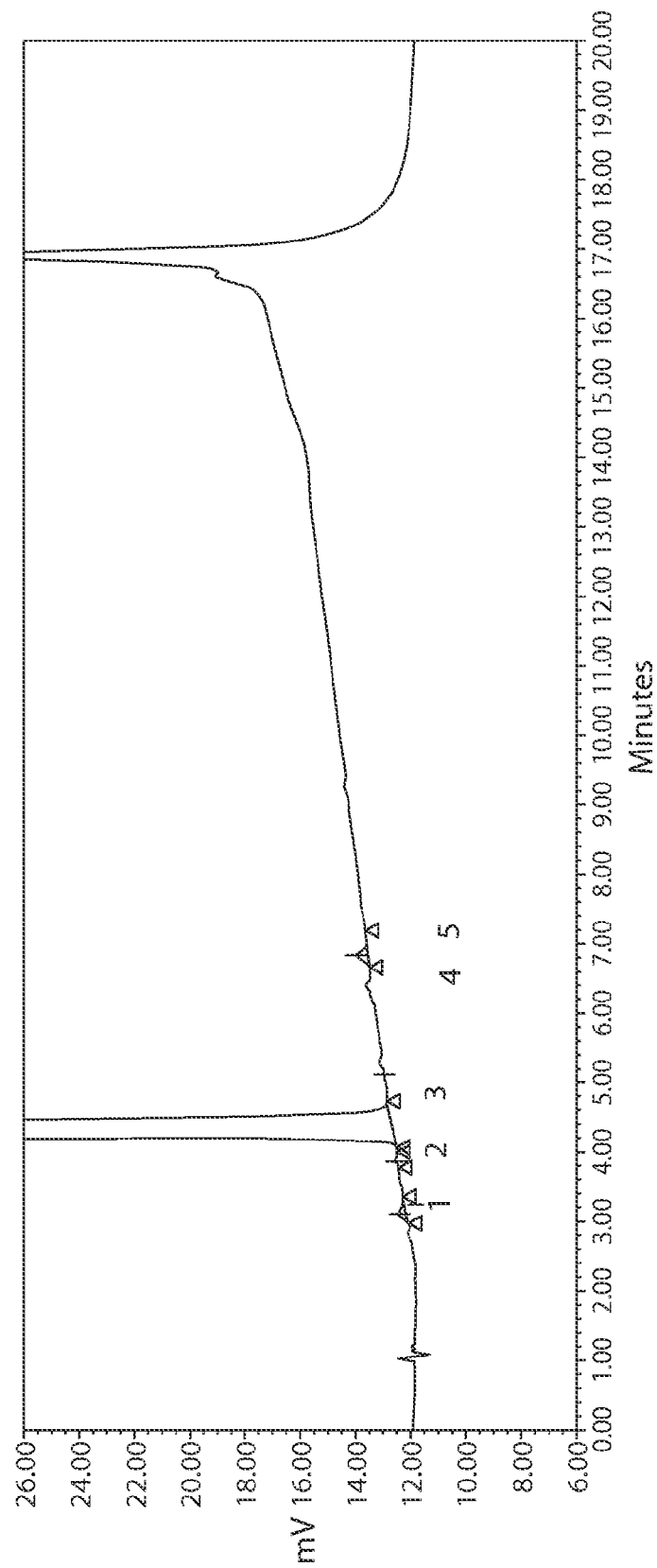
FIG. 1 is a graph depicting methylnaltrexone degradation products eluting from a column at time zero (peak Nos. 1, 2 and 4 are degradation products; peak No 4 is methylnaltrexone; peak no 5. O-methylnaltrexone bromide).

Applicants have discovered that during the autoclaving process, methylnaltrexone in aqueous solution tends to degrade to a surprising extent. The amount of degradation resulting from simple autoclaving (122° C., 15 lbs. pressure for 20 min.) can be as high as 10%. The degradation products are depicted in FIG. 1, and appear to include at least two predominant degradants having relative retention times (RRT) of 0.72 (2.828 minutes) and 0.89 (3.435 minutes) and, with other minor forms as can be observed. The degradant identified by the 0.72 RRT peak appears in small amounts, 0.074, immediately upon dissolving the methylnaltrexone into solution and increases overtime with storage or autoclaving 0.25%. The degradant identified by the 0.89 RRT peak appears only after storage over time or after autoclaving (<0.05% and 0.724%, respectively). Applicants also have discovered that methylnaltrexone is unstable in aqueous solutions when stored at room temperature or even at 4° C. for significant (but commercially necessary) periods of time such as 6 months, 12 months or even two years. Degradation occurs without regard to whether the aqueous solution was previously autoclaved or filter sterilized. It would be desirable to stabilize formulations of methylnaltrexone such that following the autoclaving process or following storage (or both autoclaving and storage), the amount of the total degradation products would be less than 2.0%, 1.5%, 1.0%, 0.5%, 0.25%, and even 0.125%.

The invention provides stable formulations of methylnaltrexone. By stable solutions of methylnaltrexone, it is meant that following autoclaving at 122° C., 15 lbs. pressure for 20 minutes, the methylnaltrexone degradation products resulting from such conditions are not more than 2% of the total methylnaltrexone present in a given solution. By stable solution of methylnaltrexone, it also is meant that following storage of an unautoclaved solution at room temperature for twelve months, the methylnaltrexone degradation products resulting from such conditions are not more than 2% of the total methylnaltrexone present in a given solution. By stable solutions of methylnaltrexone, it is also meant that following storage of an unautoclaved solution at room temperature for two months, the methylnaltrexone degradation products resulting from such conditions are not more than 1.0% of the total methylnaltrexone present in a given solution. By stable lyophilized formulations of methylnaltrexone, it is meant that following lyophilization and storage at room temperature of methylnaltrexone for two months, and their reconstitution in water the methylnaltrexone degradation products resulting from such conditions are not more than 1.0% of the total methylnaltrexone present in a given solution.

It was surprisingly discovered that pH alone can solve the problem of excessive methylnaltrexone degradation products. In particular, it was discovered that when the pH of a methylnaltrexone solution containing 2 mg/mL of methylnaltrexone was at about 4.25 pH or less, there was a steep drop-off in the amount of methylnaltrexone degradation products following autoclaving. When the pH of the solution containing methylnaltrexone was adjusted to between 3.5 and 4.0, then the total percentage of degradants fell below 2%, and in certain instances even below 1.39%. When the pH was adjusted to between 3.0 and 3.5, the percentage of total degradants dropped to about 0.23% after autoclaving. It was also noted that there was a significant drop, before a plateau, when the pH of the methylnaltrexone solution was brought to below 6.0 prior to autoclaving. Adjusting pHs to between 4.25 and 6 was not sufficient to produce stable formulations of methylnaltrexone (through the adjustment of pH alone). As will be seen below, however, manipulating other parameters in concert with pH resulted in stable formulations of methylnaltrexone anywhere in a range from a pH of 2.0 to 6.0. The benefits of a low pH on the stability of methylnaltrexone formulations persisted in the presence of chelating agents, isotonicity agents, buffering agents, and antioxidants. Thus, the invention in one aspect provides stable formulations of methylnaltrexone in solution, wherein the pH is below 4.25, preferably between 3.0 and 4.0, and most preferably between 3.0 and 3.5.

Applicants also noted that despite setting the pH of a methylnaltrexone solution at points between 3.0 and 6.0 using a pH-adjusting acid or pH-adjusting base prior to autoclaving and despite the benefits obtained from lower pH, the pH of the autoclaved sample drifted almost immediately to about 7.0. It was therefore tested, in particular, whether buffering agents could eliminate the pH drift that resulted from autoclaving without negatively affecting the ability to protect against heat degradation resulting from autoclaving. Applicants discovered that buffering agents indeed could be employed to stabilize the pH of methylnaltrexone solutions throughout the autoclaving process without permitting degradation products to exceed acceptable minimums. Buffers were used in concentrations ranging from 0.25 mM to 25 mM. Acceptable levels of degradation products were obtained at all buffer concentrations tested. It was noted, however, that citrate buffer had properties more desirable than those of acetate buffer. In particular, the addition of citrate buffer did not seem to alter in any material respects the amount of degradation products resulting from autoclaving the methylnaltrexone solution, resulting in less than 0.23% of degradation products at pH of 3.5. The addition of acetate buffer, however, appeared to increase somewhat the amount of methylnaltrexone degradation products, although not to unacceptable levels, resulting in less than 1.39% of degradation products at pH of 3.6. Nonetheless, citrate buffer surprisingly is preferable to acetate buffer. The preferred citrate buffer range is between about 2 and 5 mM.

Buffers in general are well known to those of ordinary skill in the art. Buffer systems include citrate buffers, acetate buffers, borate buffers, and phosphate buffers. Examples of buffers include citric acid, sodium citrate, sodium acetate, acetic acid, sodium phosphate and phosphoric acid, sodium ascorbate, tartartic acid, maleic acid, glycine, sodium lactate, lactic acid, ascorbic acid, imidazole, sodium bicarbonate and carbonic acid, sodium succinate and succinic acid, histidine, and sodium benzoate and benzoic acid.

Applicants also discovered, surprisingly, that a chelating agent alone was capable of reducing the amount of degradation products to acceptable levels. In particular, pH was not adjusted and disodium edetate was added at concentrations of 0.01, 0.1, 0.25, 0.5, 0.75, and 1.0 mg/mL. The disodium edetate stabilized methylnaltrexone against heat degradation in a concentration-dependent manner. As little as 0.01 mg/mL had a substantial effect on the amount of degradants, yielding approximately 2.3% total degradants. A concentration of 0.1 mg/mL resulted in under 1.5% total degradants. There was a critical point at approximately 0.3-0.4 mg/mL where the total degradants became slightly under 0.5% and leveled off with increasing amounts of disodium edetate. Thus, disodium edetate alone was sufficient to render stable an unbuffered solution of methylnaltrexone with no adjustment to pH. This was a surprising result.

Applicants believe that the result is not limited to disodium edetate. Instead, other chelating agents well known to those of ordinary skill in the art will be useful according to the invention. Chelating agents are chemicals which form water soluble coordination compounds with metal ions in order to trap or remove the metal irons from solution, thereby avoiding the degradative effects of the metal ions. Chelating agents include ethylenediaminetetraacetic acid (also synonymous with EDTA, edetic acid, versene acid, and sequestrene), and EDTA derivatives, such as dipotassium edetate, disodium edetate, edetate calcium disodium, sodium edetate, trisodium edetate, and potassium edetate. Other chelating agents include citric acid and derivatives thereof. Citric acid also is known as citric acid monohydrate. Derivatives of citric acid include anhydrous citric acid and trisodiumcitrate-dihydrate. Still other chelating agents include niacinamide and derivatives thereof and sodium desoxycholate and derivatives thereof. A synergistic effect of pH and disodium edetate was also observed. At pH 3-3.5, in the presence of citrate buffer (25 mM), and 0.01 mg/mL disodium edetate, the total degradants after autoclaving amounted to less than 0.4%. Under the same conditions, except increasing the concentration of disodium edetate to 1 mg/mL, there was no detectable difference. That is, the degradants were on the order of approximately 0.4% after autoclaving. The circumstance, however, differed when pH was adjusted upwardly to between 6.0 and 7.0 in an unbuffered system. In particular, at a pH adjusted upwardly to between 6.0 and 7.0, the total degradants were above 3-6% at a concentration of 0.01 mg/mL disodium edetate and approximately 2.8% at 1.0 mg/mL disodium edetate. This at first glance appears anomalous with the results described above, where disodium edetate alone was sufficient to bring total degradants under 0.5% at concentrations above approximately 0.3 disodium edetate mg/mL. It was discovered, however, that the increase in degradation was due to the addition of a pH-adjusting base to the solution containing methylnaltrexone to upwardly adjust the pH to 6.0~7.0. Therefore, it was discovered unexpectedly that the addition of a pH-adjusting base, such as sodium hydroxide, to a solution containing methylnaltrexone should be avoided in order to minimize the presence of degradants.

The same results were achieved through a combination of acetate buffer and disodium edetate at 0.01 mg/mL and 1.0 mg/mL, although, once again, citrate buffer seemed to work surprisingly better than acetate buffer in protecting methylnaltrexone to from heat degradation. Higher levels of disodium edetate in the presence of acetate buffer could compensate, however, for the differential effect that was observed when using citrate buffer versus acetate buffer. It is to be noted that citrate buffer also is a chelating agent, which might contribute to its apparent superior properties. However, there was no concentration-dependent stabilization due to citrate buffer and it would appear that the chelating effect of citrate is not wholly responsible for the differential effects observed between citrate buffer and acetate buffer.

Applicants also believe that antioxidants will be useful according to the invention. Antioxidants are substances capable of inhibiting oxidation by removing free radicals from solution. Antioxidants are well known to those of ordinary skill in the art and include materials such as ascorbic acid, ascorbic acid derivatives (e.g., ascorbylpalmitate, ascorbylstearate, sodium ascorbate, calcium ascorbate, etc.), butylated hydroxy anisole, buylated hydroxy toluene, alkylgallate, sodium meta-bisulfate, sodium bisulfate, sodium dithionite, sodium thioglycollic acid, sodium formaldehyde sulfoxylate, tocopherol and derivatives thereof, (d-alpha tocopherol, d-alpha tocopherol acetate, dl-alpha tocopherol acetate, d-alpha tocopherol succinate, beta tocopherol, delta tocopherol, gamma tocopherol, and d-alpha tocopherol polyoxyethylene glycol 1000 succinate) monothioglycerol, and sodium sulfite. Such materials are typically added in ranges from 0.01 to 2.0%.

The pharmaceutical preparations of the invention also may include isotonicity agents. This term is used in the art interchangeably with iso-osmotic agent, and is known as a compound which is added to the pharmaceutical preparation to increase the osmotic pressure to that of 0.9% sodium chloride solution, which is iso-osmotic with human extracellular fluids, such as plasma. Preferred isotonicity agents are sodium chloride, mannitol, sorbitol, lactose, dextrose and glycerol.

Optionally, the pharmaceutical preparations of the invention may further comprise a preservative. Suitable preservatives include but are not limited to: chlorobutanol (0.3-0.9% WN), parabens (0.01-5.0%), thimerosal (0.004-0.2%), benzyl alcohol (0.5-5%), phenol (0.1-1.0%), and the like.

In view of the success achieved with disodium edetate alone in an unbuffered system, it would have been expected that stable formulations could be prepared at virtually any pH simply by optimizing the various potential methylnaltrexone degradation inhibiting agents. Such agents include those as described above, that is, chelating agents, buffering agents, antioxidants, and the like. It was discovered, however, that stable formulations of methylnaltrexone in solution could not be obtained with such degradation inhibiting agents at pHs above 6. Thus, in one aspect of the invention, stable pharmaceutical preparations containing methylnaltrexone in solution are permitted, wherein the solution further includes an agent selected from the group consisting of a chelating agent, a buffering agent, an antioxidant, and combinations thereof, provided that the solution has a pH ranging from between 2 to 6.

The stable pharmaceutical preparations of the invention are stable not only to heat degradation resulting from autoclaving, but also to other sterilization processes used during manufacturing. Sterilization processes or techniques as used herein include aseptic techniques such as one or more filtration (0.45 or 0.22 micron filters) steps, autoclaving, and a combination of filtration and autoclaving. They also are stable to long term storage. The stable formulations of the invention are stable for at least six months at temperatures of 30° C. or less, preferably a range from 5° C. to 30° C., and, more preferably, they are stable at a temperature above 15° C. for at least six months. More particularly, the stable pharmaceutical preparations are stable for periods of at least six months, at least twelve months, and even at least twenty-four months at about room temperature or 25° C. Such preparations remain substantially free of methylnaltrexone degradation products, that is, such solutions contain less than 2% methylnaltrexone degradation products compared to the total amount of methylnaltrexone in the solution.

Applicants also discovered, surprisingly, that lyophilizing conditions could dramatically affect the amount of methylnaltrexone degradation products. The pharmaceutical preparations of the invention therefore may advantageously include cryoprotective agents, which protect methylnaltrexone from the harmful effects of freezing. Such agents also can prevent caking and flaking, which can be problematic in reconstituting a solution and in manufacturing processing. Important cryoprotecting agents are mannitol, lactose, sucrose, polyethylene glycol and polyvinyl pyrrolidine. Most preferred is mannitol. It is believed that cryoprotecting agents which result in a reconstitution pH of 6.0 and higher or which are basic will contribute also to degradation of methylnaltrexone due to pH effects discussed above. Thus, preferred cryoprotecting agents are those which, together with the other components of the formulation, result in a Do pH in the preferred ranges described above. Preferably, the cryoprotecting agent is neutral or acidic.

The amount of methylnaltrexone in the solution is effective to treat completely, ameliorate, or even prevent conditions associated with activation of endogenous opioid receptors, in particular, peripheral opioid receptors such as mu opioid receptors. Such conditions include nausea, emesis, dysphoria, pruritus, urinary retention, ileus, post-operative ileus, post-partumileus, parallytic ileus, bowel hypomotility, constipation, gastric hypomotility, delayed gastric emptying, decreased biliary secretion, decreased pancreatic secretion, biliary spasm, increased sphincter tone, cutaneous flushing, impaction, sweating, inhibition of gastrointestinal motility, inhibition of gastric emptying, gastrointestinal dysfunction, incomplete evacuation, bloating, abdominal distention, increased gastroesophageal reflux, hypotension, bradycardia, irritable bowel syndrome, or immunosuppression. One important use is in the treatment of constipation, i.e., less than one bowel movement in 3 days or less than 3 bowel movements in a week.

In any of the foregoing embodiments, the methylnaltrexone can be present in an amount sufficient to accelerate discharge from hospital post-surgery, accelerate bowel sounds after surgery, or induce laxation. Such amounts are well known to those of ordinary skill in the art and are described in the literature, including the patents listed in the background of the invention. The methylnaltrexone may also be in a salt form, including the bromide, chloride, iodide, carbonate, and sulfate salts of methylnaltrexone.

Patients treatable with the formulations of the invention include those receiving opioids including opioids for pain, cancer or surgical patients, immunosuppressed or immunocompromised patients (including HIV infected patients), patients with advanced medical illness, terminally ill patients, patients with neuropathies, patients with rheumatoid arthritis, patients with osteoarthritis, patients with chronic pack pain, patients with spinal cord injury, patients with chronic abdominal pain, patients with chronic pancreatic pain, patients with pelvic perineal pain, patients with fibromyalgia, patients with chronic fatigue syndrome, patients with migraine or tension headaches, patients on hemodialysis, and patients with sickle cell anemia.

The pharmaceutical preparations of the invention also can include an opioid. The therapeutic use of opioids is well known and, again, is described in both the literature and the patents mentioned above. Opioids include alfentanil, anileridine, asimadoline, bremazocine, burprenorphine, butorphanol, codeine, dezocine, diacetylmorphine (heroin), dihydrocodeine, diphenoxylate, fedotozine, fentanyl, funaltrexamine, hydrocodone, hydromorphone, levallorphan, levomethadyl acetate, levorphanol, loperamide, meperidine (pethidine), methadone, morphine, morphine-6-glucoronide, nalbuphine, nalorphine, opium, oxycodone, oxymorphone, pentazocine, propiram, propoxyphene, remifentanyl, sufentanil, tilidine, trimebutine, and tramadol.

It should be understood that the pharmaceutical preparations of the invention will typically be held in bottles, vials, ampoules, infusion bags, and the like, any one of which may be sparged to eliminate oxygen or purged with nitrogen. In some embodiments, the bottles vials and ampoules are opaque, such as when amber in color. Such sparging and purging protocols are well known to those of ordinary skill in the art and should contribute to maintaining the stability of the pharmaceutical preparations. The pharmaceutical preparations also, in certain embodiments, are expected to be contained within syringes.

Figure 3:
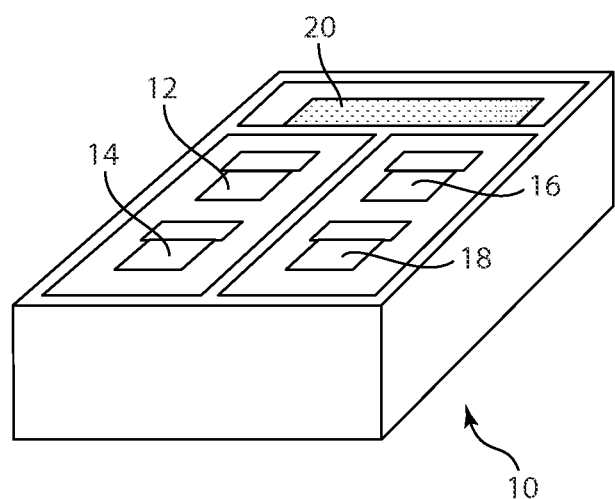
FIG. 3 is a schematic representation of a kit according to the invention containing the formulations described herein.

According to another aspect of the invention, kits also are provided. Referring to FIG. 3, a kit 10 is depicted. The kit 10 includes a pharmaceutical preparation vial 12, a pharmaceutical preparation diluent vial 14, an opioid vial 16, and an opioid diluent vial 18. The kit also includes instructions 20. The vial 14 containing the diluent for the pharmaceutical preparation is optional. The vial 14 contains a diluent such as physiological saline for diluting what could be a concentrated solution of methylnaltrexone contained in vial 12. The instructions can include instructions for mixing a particular amount of the diluent with a particular amount of the concentrated pharmaceutical preparation, whereby a final formulation for injection or infusion is prepared. The instructions may include instructions for use in a patient controlled analgesia (PCA) device. Likewise, the kit optionally contains an opioid in the opioid vial 16, which also optionally may be in a concentrated form. The optional vial 18 contains a diluent for a concentrated opioid. The instructions also may include instructions for mixing the opioid with the pharmaceutical preparation and/or diluting the opioid with the opioid diluent contained in the opioid diluent vial 18. The instructions, therefore, would take a variety of forms depending on the presence or absence of diluent and opioid. The instructions 20 can include instructions for treating a patient with an effective amount of methylnaltrexone. It also will be understood that the containers containing the pharmaceutical preparation, whether the container is a bottle, a vial with a septum, an ampoule with a septum, an infusion bag, and the like, can contain indicia such as conventional markings which change color when the pharmaceutical preparation has been autoclaved or otherwise sterilized.

The pharmaceutical preparations of the invention, when used in alone or in cocktails, are administered in therapeutically effective amounts. A therapeutically effective amount will be determined by the parameters discussed below; but, in any event, is that amount which establishes a level of the drug(s) effective for treating a subject such as a human subject, having one of the conditions described herein. An effective amount means that amount alone or with multiple doses, necessary to delay the onset of, inhibit completely or lessen the progression of or halt altogether the onset or progression of the condition being treated. When administered to a subject, effective amounts will depend, of course, on the particular condition being treated; the severity of the condition; individual patient parameters including age, physical condition, size and weight; concurrent treatment; frequency of treatment; and the mode of administration. These factors are well known to those of ordinary skill in the art and can be addressed with no more than routine experimentation. It is preferred generally that a maximum dose be used, that is, the highest safe dose according to sound medical judgment.

The pharmaceutical preparations of the present invention may include or be diluted into a pharmaceutically-acceptable carrier. The term "pharmaceutically-acceptable carrier" as used herein means one or more compatible solid, or semi-solid or liquid fillers, diluents or encapsulating substances which are suitable for administration to a human or other mammal such as a dog, cat, horse, cow, sheep, or goat. The term "carrier" denotes an organic or inorganic ingredient, natural or synthetic, with which the active ingredient is combined to facilitate the application. The carriers are capable of being commingled with the preparations of the present invention, and with each other, in a manner such that there is no interaction which would substantially impair the desired pharmaceutical efficacy or stability. Carriers suitable for oral, subcutaneous, intravenous, intramuscular, etc. formulations can be found in Remington's Pharmaceutical Sciences, Mack Publishing Company, Easton, Pa.

A variety of administration routes are available. The particular mode selected will depend of course, upon the particular drug selected, the severity of the disease state being treated and the dosage required for therapeutic efficacy. The methods of this invention, generally speaking, may be practiced using any mode of administration that is medically acceptable, meaning any mode that produces effective levels of the active compounds without causing clinically unacceptable adverse effects. Such modes of administration include oral, rectal, sublingual, topical, nasal, transdermal or parenteral routes. The term is "parenteral" includes subcutaneous, intravenous, intramuscular, or infusion.

Dosage may be adjusted appropriately to achieve desired drug levels, locally or systemically. Generally, daily oral doses of active compounds will be from about 0.1 mg/kg per day to 30 mg/kg per day. It is expected that IV doses in the range of 0.01-1.00 mg/kg will be effective. In the event that the response in a subject is insufficient at such doses, even higher doses (or effective higher doses by a different, more localized delivery route) may be employed to the extent that patient tolerance permits. Continuous IV dosing over, for example, 24 hours or multiple doses per day also are contemplated to achieve appropriate systemic levels of compounds. Preferred subcutaneous doses for chronic opioid users to induce laxation are 0.1-0.3 mg/kg, and preferred oral doses for the same patient population are 1.0-3.0 mg/kg. Preferred IV doses to treat post operative ileus are 0.15 mg/kg.

The invention also involves methods for preparing autoclaved pharmaceutical preparations that have concentrations of methylnaltrexone degradation products that do not exceed 2% of the methylnaltrexone or salt thereof in the preparation. Aqueous solutions of methylnaltrexone are prepared. A pH-adjusting acid is added to adjust the pH to 4.25 or less, preferably to a range of between 3.0 and 3.5. The solution is then autoclaved according to standard procedures. One such procedure involves autoclaving at 122° C. and 15 pounds of pressure for 20 minutes. The pharmaceutical preparation can contain any one, any combination of or all of a chelating agent, an isotonicity agent, a buffering agent, an antioxidant, a cryoprotective agent, and an opioid. According to another aspect of the invention, a pharmaceutical preparation containing methylnaltrexone in a aqueous solution is prepared by combining a chelating agent with the methylnaltrexone solution and then autoclaving the solution. The aqueous solution of methylnaltrexone may contain any one of, any combination of or all of a buffering agent, an antioxidant, an isotonicity agent and an opioid.

According to yet another aspect of the invention, a pharmaceutical preparation containing methylnaltrexone in a lyophilized formulation is prepared by combining a cryoprotective agent, such as mannitol, with the methylnaltrexone formulation. The lyophilized preparation may also contain any one of, any combination of, or all of a buffering agent, an antioxidant, an isotonicity agent and an opioid.

The invention also involves methods of inhibiting the formation of methylnaltrexone degradation products in a solution containing methylnaltrexone by combining any one of, any combination of or all of a chelating agent, a buffering agent and an antioxidant with methylnaltrexone or salt thereof in solution. In one preferred embodiment, the aqueous solution containing the chelating agent, buffering agent and/or antioxidant is first prepared, then a powdered source of methylnaltrexone or salt thereof is dissolved into the aqueous solution.

The invention also involves methods of inhibiting the formation of methylnaltrexone degradation products in a gel containing methylnaltrexone by combining any one of, any combination of or all of a chelating agent, a buffering agent and an antioxidant with methylnaltrexone or salt thereof in a gel matrix. In one preferred embodiment, the gel containing the chelating agent, buffering agent and/or antioxidant is first prepared, then a powdered source of methylnaltrexone or salt thereof is dissolved into the gel. As used herein, solution embraces gels.

The pharmaceutical preparations of the invention may be provided in particles. Particles as used herein means nano or microparticles (or in some instances larger) which can consist in whole or in part of the peripheral opioid antagonists or the other therapeutic agent(s) as described herein. The particles may contain the therapeutic agent(s) in a core surrounded by a coating, including, but not limited to, an enteric coating. The therapeutic agent(s) also may be dispersed throughout the particles. The therapeutic agent(s) also may be adsorbed into the particles. The particles may be of any order release kinetics, including zero order release, first order release, second order release, delayed release, sustained release, immediate release, and any combination thereof, etc. The particle may include, in addition to the therapeutic agent(s), any of those materials routinely used in the art of pharmacy and medicine, including, but not limited to, erodible, nonerodible, biodegradable, or nonbiodegradable material or combinations thereof. The particles may be microcapsules which contain the antagonist in a solution or in a semi-solid state. The particles may be of virtually any shape.

Both non-biodegradable and biodegradable polymeric materials can be used in the manufacture of particles for delivering the therapeutic agent(s). Such polymers may be natural or synthetic polymers. The polymer is selected based on the period of time over which release is desired. Bioadhesive polymers of particular interest include bioerodible hydrogels described by H. S. Sawhney, C. P. Pathak and J. A. Hubell in *Macromolecules*, (1993) 26:581-587, the teachings of which are incorporated herein. These include polyhyaluronic acids, casein, gelatin, glutin, polyanhydrides, polyacrylic acid, alginate, chitosan, poly(methyl methacrylates), poly(ethyl methacrylates), poly(butylmethacrylate), poly(isobutyl methacrylate), poly(hexylmethacrylate), poly (isodecyl methacrylate), poly(lauryl methacrylate), poly (phenyl methacrylate), poly(methyl acrylate), poly(isopropyl acrylate), poly(isobutyl acrylate), and poly(octadecyl acrylate).

The invention also provides methods for preparing stable pharmaceutical preparations containing aqueous solutions of methylnaltrexone or salts thereof to inhibit formation of methylnaltrexone degradation products. A solution is provided that contains methylnaltrexone or salts thereof and at least one methylnaltrexone inhibiting agent. The solution is processed under at least one sterilization technique prior to and/or after terminal filing the solution in the sealable container to form a stable pharmaceutical preparation, wherein the method is carried out without the addition of a pH-adjusting base to the solution.

EXAMPLES

Example 1

Manufacturing Process for a Pharmaceutical Formulation of Methylnaltrexone

A manufacturing process can be outlined as follows:
1. Add required amount of water for injection (~80% or final volume) to a stainless steel tank.
2. Add chelating agent to the tank and stir till dissolved.
3. Add buffering agent to the tank and stir till dissolved.
4. Add methylnaltrexone to the tank and stir till dissolved.
5. Add isotonicity agent to the tank and stir till dissolved.
6. Adjust the pH of the solution to pH 3.25.
7. Add water for injection to increase the volume to the required amount.
8. Transfer material to supply pressure vessel.
9. Sterile filter into a sterile stainless steel pressure vessel.
10. Fill into bottles/vials, purge with nitrogen and then stopper the bottles/vials.
11. Sterilize the filled vials by autoclaving.

Exact Amount of Excipients to be Used:

| | |
|---|---|
| Disodium edetate = 0.75 mg/ml | Added in step 2 |
| Sodium Citrate = 0.199 mg/ml | Added in step 3 |
| Citric acid = 0.35 mg/ml | Added in step 3 |
| Sodium Chloride = 8.5 mg/ml | Added in step 5 |

The order of addition of excipients is described above. Steps 2 to 5 can take place in any order.

When all excipients and drug have been added, step 6, pH of the solution is adjusted by addition of acid. If a buffering agent is used in the solution, pH adjustment may not be required.

There are no specifics on the temperature or the stirring speed during the formulation. The temperature during formulation can be as high as 80° C.

Example 2

Preferred Manufacturing Process for a Pharmaceutical Formulation of Methylnaltrexone A preferred manufacturing process is as follows:
100 ml of 20 mg/ml solution of methylnaltrexone solutions
1. Add 80 ml of water for injection (~80% or final volume) to a stainless steel tank.
2. Add 75 mg of disodium edetate, a chelating agent, to the tank and stir till dissolved.
3. Add 19.9 mg of sodium citrate and 35 mg of citric acid (as buffering agents) to the tank and stir till dissolved.
4. Add 2000 mg of methylnaltrexone to the tank and stir till dissolved.

5. Add 850 mg of sodium chloride, an isotonicity agent, to the tank and stir till dissolved.
6. Adjust the pH of the solution if necessary.
7. Add water for injection to increase the volume to 100 ml.
8. Transfer the material to supply pressure vessel.
9. Sterile filter using a 0.22 micron filter into a sterile stainless steel pressure vessel.
10. Fill, purge with nitrogen and then stopper the bottles/vials.
11. Sterilize the filled vials by autoclaving.

Example 3

12 Month Stability of Pharmaceutical Preparation Methylnaltrexone

Methylnaltrexone (bromide salt) and its degradation products in an isotonic saline solution were tested upon manufacture of the solution (no added stabilizers, sterile filtered, not autoclaved) and upon storage at room temperature for 12 months using a Hewlett-Packard HP1100 series, HPLC system equipped with quaternary gradient pump, programmable variable wavelength UV detector and a Millennium data acquisition system. Two mobile phases were prepared as follows:

The reagents, standards and media included naltrexone methobromide as a reference standard, trifluoroacetic acid (ACS grade), acetonitrile (HPLC grade), Milli-Q water (or equivalent), and methanol (HPLC grade). The solutions were prepared as follows. Mobile phase A (85:15:0.1) (water:methanol:trifluoroacetic acid): 850 mL of Milli-Q water was added to a suitable container, to which 150 mL of methanol and 1.0 mL of trifluoroacetic acid were added. The solution was mixed well and allowed to equilibrate to room temperature. The solution was degassed by helium sparge. Mobile phase B (methanol): Methanol was added to a suitable container and degas sed by helium sparge.

Instrumental Conditions

Analytical Column: Metachem Inertsil ODS3, 5 μm, 150×4.6 mm or equivalent

Mobile phase: A mixture of Mobile phase A and B is used as shown in Table I:

TABLE I

| Time (minutes) | % A | % B |
|---|---|---|
| 0 | 100 | 0 |
| 12 | 65 | 35 |
| 15 | 35 | 65 |
| 15.1 | 100 | 0 |
| 20 | 100 | 0 |

Column temperature: 50° C.
Detection: UV at 280 nm
Injection volume: 20 μL
Run time: 20 minutes
Flow rate: 1.5 mL/minute
Quantitation: Peak area responses
Results:
20 mg/ml saline drug product lot CTM-02085

| Peak No. | | Initial | | 12 months | |
|---|---|---|---|---|---|
| | | RRT | % Degradants | RRT | % Degradants |
| 1 | degradation product | 0.72 | 0.07 | 0.74 | 0.25 |
| 2 | degradation product | 0.89 | <0.05 | 0.89 | 0.72 |

-continued

| Peak No. | | Initial | | 12 months | |
|---|---|---|---|---|---|
| | | RRT | % Degradants | RRT | % Degradants |
| 3 | methylnaltrexone | 1.00 | 99.7 | 1.00 | 98.6 |
| 4 | degradation product | 1.48 | 0.06 | 1.40 | 0.16 |
| 5 | O-Methylnaltrexone Bromide (process impurity) | 1.57* | 0.17 | 1.54* | 0.17 |

Samples from the methylnaltrexone saline formulation (not autoclaved) were analyzed for methylnaltrexone degradation products before and after storage for 12 months at 25° C.

The starting material was analyzed by HPLC. As shown in FIG. 1, methylnaltrexone is a peak having an RRT of 1.0 (4.364 minutes). An additional peak was identified as O-methyl naltrexone methobromide, RRT about 1.57 (6.868 minutes). The O-methyl-naltrexone is not a degradant of methylnaltrexone but a result from the methylnaltrexone (drug substance) manufacturing process.

Figure 2:
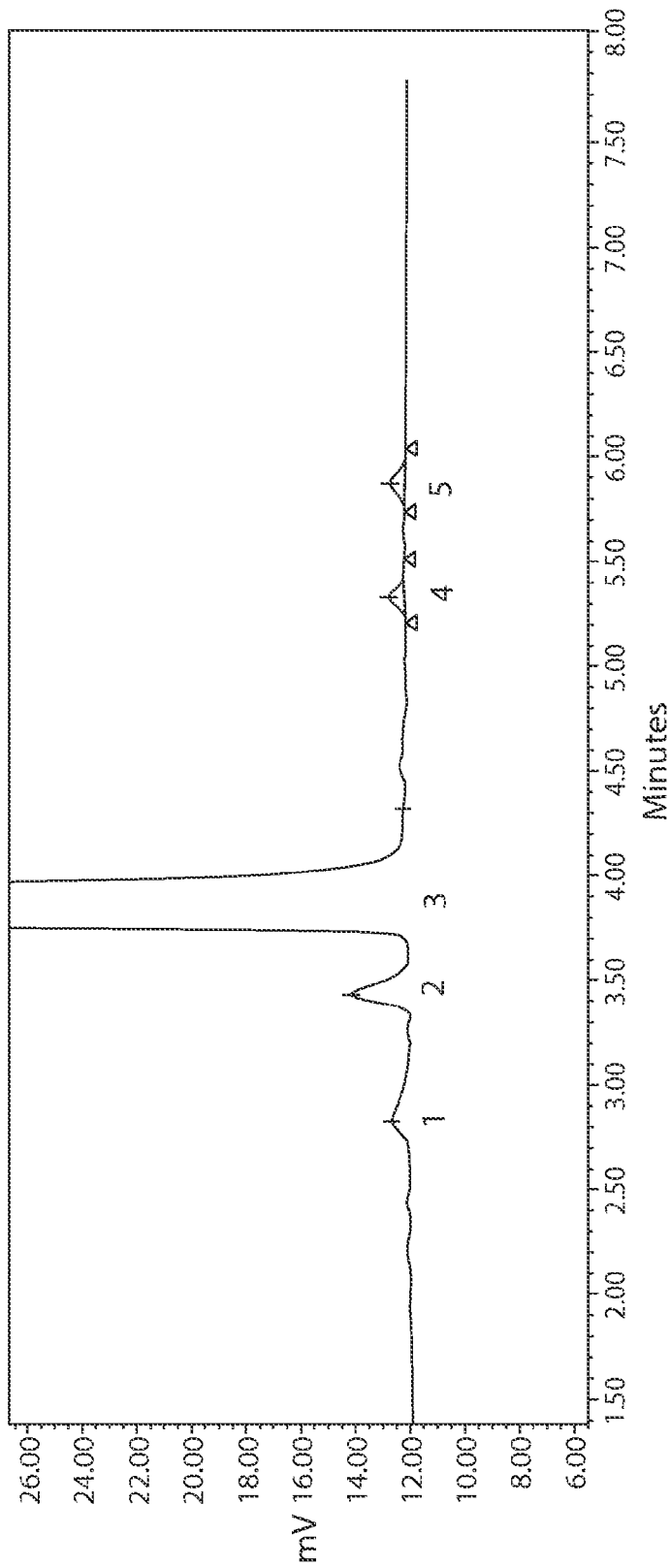
FIG. 2 is a graph depicting methylnaltrexone degradation products eluting from a column at 12 months (peak Nos. 1, 2 and 4 are degradation products; peak No 4 is methylnaltrexone; peak no 5. O-methylnaltrexone bromide).

The material stored for 12 months was similarly analyzed by HPLC. The chromatogram is shown in FIG. 2.

As in the starting material, the HPLC analysis of the sample stored for 12 months showed methylnaltrexone RRT of 1.00 (3.839 minutes), O-methyl-methylnaltrexone RRT of about 1.53 (5.866 minutes). However, HPLC analysis revealed that the methylnaltrexone saline formulation which was stored for 12 months had at least three degradation products formed during the manufacturing or during storage of the finished drug product. The degradant peak RRT's were approximately 0.74 (2.828 minutes), 0.89 (3.435 minutes) and 1.40 (5.326 minutes).

HPLC analysis was also conducted, prior to storage, on a methylnaltrexone solution manufactured using an isotonic saline solution (no added stabilizers), sterile filtered, and autoclaved. This saline, autoclaved solution contained the degradation products formed during manufacturing or storage, as described above (data not shown).

Example 4

Preparation of a Subcutaneous Formulation

The degradation products seen with very low citrate level were the same as those seen with normal saline solution. These low citrate formulas were autoclaved and after three months the amount of degradation products seen were less than 0.1% for each degradation product. The formula used for the citrate/EDTA formulation is listed below:

| | mg/mL |
|---|---|
| Methynaltrexone | 30 mg |
| Sodium Chloride | 4 mg |
| Citric acid | 0.0875 mg |
| Trisodium Citrate | 0.0496 mg |
| Disodium edetate | 0.75 mg |
| Water for injection | q.s. to 1 gram |

The pH of this solution is 3.5 and can withstand autoclaving process.

Example 5

Manufacturing Process for a Lyophilized Pharmaceutical Formulation of Methylnaltrexone The lyophilization cycle listed below is standard procude well known to one of ordinary skill in the art. This cycle was used for the preparation of lyophilized preparation of methylnaltrexone analyzed in Examples 6 and 7.
1. Load chamber at room temperature (20-25 C)
2. Lower shelf temp to −45 degrees C. at 1.0 degrees C/min
3. Hold shelf temp at −45 for 120 minutes
4. When condenser is below −50 degrees C., evacuate the chamber to 100-125 mt.
5. Ramp shelf to −20 degrees C. at 0.5 degrees C/min.
6. Hold at −20 degrees C. for 16 hours
7. Ramp shelf to +27 degrees C. at 0.10 degrees C/min
8. Hold for a minimum of 8 hours. Maintain chamber pressure at 100-125 mt for the entire cycle.
9. Restore chamber to 11.0 PSIA + or −1.0 with sterile filtered Nitrogen and then seat the closures (2" Hg), then bleed to atmospheric pressure with Nitrogen to unload.

Example 6

Stability of Lyophilized Formulations of Methylnaltrexone

The following data reports the stability of lyophilized formulations of methylnaltrexone using different cryoprotecting agents.

| Cryoprotecting Agent | pH | total degradation products |
|---|---|---|
| Mannitol | 5.0 | 0.34% |
| Polyvinyl pyrrolidone | 4.1 | 0.37% |
| Polyethylene glycol | 5.7 | 0.44% |
| Histidine | 7.4 | 0.55% |

Example 7

Stability of Lyophilized Formulations of Methylnaltrexone

The following data reports the stability of lyophilized formulations of methylnaltrexone in comparison to buffered formulations.
Amount of Total Related Substances at Various Stages of Manufacturing

| | 1 | 2 | 3 | 4 | 5 | 6 |
|---|---|---|---|---|---|---|
| Key Ingredient | Monothio-glycerol | Citrate Buffer pH 3.5 | Citrate Buffer pH 5 | Acetate Buffer pH 3.6 | Lyophilized using Mannitol | Lyophilized using Lactose |
| Unautoclaved | 0.13 | 0.12 | 0.16 | 0.20 | 0.14 | 0.12 |
| Autoclaved | 0.91 | 0.23 | 0.61 | 1.39 | n/a | n/a |
| Stability (2 mths at room temp) | 1.10 | 0.16 | 0.48 | 1.26 | 0.15 | 0.15 |

It should be understood that various changes and modifications to the preferred embodiments described herein will be apparent to those of ordinary skill in the art. Such changes and modifications can be made without departing from the spirit and scope of this invention without diminishing its advantages. It is therefore intended that such changes and modifications, including equivalents, be covered by the appended claims. All of the patents, patent applications and references listed herein are incorporated by reference in their entirety.

We claim:

1. A stable pharmaceutical preparation comprising a solution of methylnaltrexone or salt thereof and a chelating agent consisting of EDTA, or a derivative thereof, wherein the solution has a pH ranging from about 3.0 to 4.0.

2. The pharmaceutical preparation of claim 1, wherein less than 1% methylnaltrexone degradation products form following 12 months stored at about room temperature, relative to the total methylnaltrexone present in the solution.

3. The pharmaceutical preparation of claim 1, wherein less than 1% methylnaltrexone degradation products form following 24 months stored at about room temperature, relative to the total methylnaltrexone present in the solution.

4. The pharmaceutical preparation of claim 3, wherein the concentration of methylnaltrexone or salt thereof ranges from 0.01 to 100 mg/ml.

5. The pharmaceutical preparation of claim 4, wherein the concentration of methylnaltrexone or salt thereof ranges from 1.0 to 50.0 mg/ml.

6. The pharmaceutical preparation of claim 5, wherein the concentration of methylnaltrexone or salt thereof is about 20 mg/ml.

7. The pharmaceutical preparation of claim 5, wherein the chelating agent consists of dipotassium edetate, disodium edetate, edetate calcium disodium, sodium edetate, trisodium edetate, potassium edetate, or a combination thereof.

8. The pharmaceutical preparation of claim 7, wherein the chelating agent consists of edetate calcium disodium.

9. The pharmaceutical preparation of claim 8, wherein the chelating agent concentration ranges from about 0.001 to about 100 mg/ml.

10. The pharmaceutical preparation of claim 9, wherein the chelating agent concentration ranges from about 0.1 to about 25.0 mg/ml.

11. The pharmaceutical preparation of claim 10, wherein the chelating agent concentration is about 0.1 to about 2.5 mg/ml.

12. The pharmaceutical preparation of claim 5, further comprising an isotonicity agent.

13. The pharmaceutical preparation of claim 7, further comprising an isotonicity agent.

14. The pharmaceutical preparation of claim 8, further comprising an isotonicity agent.

15. The pharmaceutical preparation of claim 5, wherein the preparation comprises a buffering agent.

16. The pharmaceutical preparation of claim 7, wherein the preparation comprises a buffering agent.

17. The pharmaceutical preparation of claim 8, wherein the preparation comprises a buffering agent.

18. The pharmaceutical preparation of claim 7, further comprising a preservative and an isotonicity agent.

19. The pharmaceutical preparation of claim 18, wherein the preparation comprises a buffering agent.

20. The pharmaceutical preparation of claim 1, wherein the preparation comprises a solution of methylnaltrexone bromide.

21. The pharmaceutical preparation of claim 1, wherein less than 2% methylnaltrexone degradation products form following 12 months stored at about room temperature, relative to the total methylnaltrexone present in the solution.

22. The pharmaceutical preparation of claim 1, wherein the preparation is processed under at least one sterilization technique.

23. The pharmaceutical preparation of claim 1, wherein the solution has a pH from about 3.0 to about 3.5.

24. The pharmaceutical preparation of claim 1, wherein the solution has a pH of about 3.5.

25. A stable pharmaceutical preparation comprising a solution of methylnaltrexone or salt thereof, EDTA or a derivative thereof, wherein the solution has a pH from about 3.0 to 4.0, and wherein the methylnaltrexone or salt thereof is the sole pharmaceutical active agent.

26. The stable pharmaceutical preparation of claim 25, wherein the solution has a pH ranging from about 3 to about 3.5.

27. The stable pharmaceutical preparation of claim 26, wherein the solution has a pH of about 3.5.

28. The pharmaceutical preparation of claim 25, wherein the pharmaceutical preparation is stable to storage for 3 months at about room temperature.

29. The pharmaceutical preparation of claim 26, wherein the pharmaceutical preparation is stable to storage for 6 months at about room temperature.

30. The pharmaceutical preparation of claim 26, wherein the pharmaceutical preparation is stable to storage for 12 months at about room temperature.

31. The pharmaceutical preparation of claim 26, wherein the pharmaceutical preparation is stable to storage for 24 months at about room temperature.

32. The pharmaceutical preparation of claim 26, wherein the concentration of methylnaltrexone or salt thereof is about 20 mg/ml.

33. The pharmaceutical preparation of claim 32, wherein the concentration of EDTA or derivative thereof ranges from about 0.3 to about 0.5 mg/ml.

34. The pharmaceutical preparation of claim 25, wherein about 1% or less methylnaltrexone degradation products form following 3 months stored at about room temperature, relative to the total methylnaltrexone present in the solution.

35. The pharmaceutical preparation of claim 27, wherein about 1% or less methylnaltrexone degradation products form following 6 months stored at about room temperature, relative to the total methylnaltrexone present in the solution.

36. The pharmaceutical preparation of claim 27, wherein about 1% or less methylnaltrexone degradation products form following 12 months stored at about room temperature, relative to the total methylnaltrexone present in the solution.

37. The pharmaceutical preparation of claim 27, wherein about 1% or less methylnaltrexone degradation products form following 24 months stored at about room temperature, relative to the total methylnaltrexone present in the solution.

38. The stable pharmaceutical preparation of claim 25, wherein the methylnaltrexone or salt thereof is methylnaltrexone bromide and is at a concentration of about 20 mg/mL, wherein the EDTA or a derivative thereof is at a concentration of about 0.3 to about 0.5 mg/ml, wherein the solution has a pH of about 3.5.

39. The stable pharmaceutical preparation of claim 38, wherein about 1% or less methylnaltrexone degradation products form following 3 months stored at about room temperature, relative to the total methylnaltrexone present in the solution.

* * * * *